(12) United States Patent
Epps et al.

(10) Patent No.: US 12,723,278 B2
(45) Date of Patent: Sep. 1, 2026

(54) NUCLEOTIDE EXTENSION CHAIN VERIFICATION

(71) Applicant: Agilent Technologies, Inc., Santa Clara, CA (US)

(72) Inventors: Jason Epps, Erie, CO (US); Joseph Guiles, Broomfield, CO (US); Todd B Kreutzian, Golden, CO (US); Steve Bunch, Berthoud, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 18/408,467

(22) Filed: Jan. 9, 2024

(65) Prior Publication Data

US 2024/0229126 A1 Jul. 11, 2024

Related U.S. Application Data

(63) Continuation of application No. PCT/US2023/010608, filed on Jan. 11, 2023.

(51) Int. Cl.

| | |
|---|---|
| ***C12Q 1/6869*** | (2018.01) |
| ***B01J 19/00*** | (2006.01) |
| ***B01L 3/00*** | (2006.01) |
| ***C12Q 1/6806*** | (2018.01) |

(52) U.S. Cl.

CPC ........ *C12Q 1/6869* (2013.01); *B01J 19/0046* (2013.01); *B01L 3/502715* (2013.01); *C12Q 1/6806* (2013.01); *B01L 2200/16* (2013.01); *B01L 2300/0627* (2013.01)

(58) Field of Classification Search

CPC ........................ B01L 3/502715; C12Q 1/6869

See application file for complete search history.

(56) References Cited

U.S. PATENT DOCUMENTS

| | | | |
|---|---|---|---|
| 2011/0137022 | A1 | 6/2011 | Michaud et al. |
| 2011/0287550 | A1 | 11/2011 | Shiea et al. |
| 2012/0100623 | A1 | 4/2012 | Timar et al. |
| 2022/0401910 | A1 | 12/2022 | Aemissegger et al. |

OTHER PUBLICATIONS

Li, Chengxi et al., "Fully Automated Fast-Flow Synthesis of Antisense Phosphorodiamidate Morpholino Oligomers," Nature Communications, vol. 12, Article No. 4396, Jul. 20, 2021, 8 pages.

PCT, "Notification of Transmittal of the International Search Report and the Written Opinion of the International Searching Authority, or the Declaration mailed on Sep. 27, 2023," Application No. PCT/US2023/010608, 11 pages.

*Primary Examiner* — Benjamin L Utech

(57) ABSTRACT

Methods and systems for synthesizing an oligonucleotide in a reaction chamber comprising a solid support. A nucleotide monomer is selected for addition to an oligonucleotide. An inlet stream comprising the selected monomer is fed to the reaction chamber (column) of the reaction chamber and conditions are provided in the reaction chamber for oligonucleotide synthesis. An outlet stream from the reaction chamber can be split and directed to the waste drain and/or to an analysis station where the eluent is analyzed by mass spectrometry (MS) to confirm the identity of the monomer fed through the inlet to the reaction chamber. Based on results from analyzing by MS, it is determined whether the outlet stream comprises the selected nucleotide monomer or a derivative thereof.

16 Claims, 18 Drawing Sheets

NUCLEOTIDE EXTENSION CHAIN VERIFICATION

CROSS-REFERENCE TO RELATED APPLICATIONS

This application is a continuation pursuant to 35 U.S.C. § 365 of International Application No. PCT/US2023/010608, filed on Jan. 11, 2023, which is incorporated herein by reference in its entirety.

FIELD OF THE INVENTION

The present disclosure relates to methods and system for synthesizing oligonucleotides, such as RNA and DNA, and for monitoring such synthesis.

BACKGROUND

Solid-phase synthesis is a valuable tool which can be used to prepare oligonucleotide products for many uses. The chemical synthesis of oligonucleotides generally occurs in a sequential fashion in which one end of the growing chain of nucleotides is attached to a solid surface, and reactive nucleotide monomers are condensed sequentially using a repetitive synthesis cycle. The first step of the synthesis cycle is generally the reaction of a protected nucleotide monomer with a hydroxyl group on the surface with a nucleoside attached to the surface. After initial coupling of the reactive phosphorus group with a hydroxyl on the surface, the steps that follow typically include capping of unreacted hydroxyl groups and then oxidation of the reactive phosphorus intermediate. The final step of the cycle is usually the deblocking of the hydroxyl group of the added nucleotide, so that it has a hydroxyl group that will couple to the next protected nucleotide monomer to be added. Upon the completion of the cycles of adding nucleotides, the desired oligonucleotide product is released from the solid phase, deprotected, and utilized in further biological applications.

A desirable oligonucleotide synthesis would provide the desired oligonucleotide product in high yield and high purity, such that the completed synthetic composition contains only the desired oligonucleotide product. It is also desirable to be able to monitor oligonucleotide synthesis in real-time or near real-time. This technique is advantageous to the current offerings and is currently not known to be present in the industry.

Alternative techniques that confirm the desired sequence of the oligonucleotide product after synthesis has finished in the synthesizer, the product taken from the synthesis column after cleavage and deprotection can be analyzed by high resolution mass spectrometry, such as (MS-MS), or by next generation sequencing (NGS). However, although MS allows to confirm the adequate molecular weight of the full-length synthetic oligonucleotide, it is not—most of the time—possible to confirm the correct sequence, ie the order of the monomers composition in the oligonucleotide full-length product. Length of the oligonucleotide (no greater than 30-mers) and chemical modifications of some monomers greatly limit access to the sequence information of the desired oligonucleotide product. Moreover, separation of the desired oligonucleotide from shorter oligonucleotides or other impurities before these approaches often requires chromatographic conditions that are laborious and time consuming. Furthermore, neither approach is conducted in real time. MS-MS technology is limited by the length of the oligonucleotide sequence and suffers severe signal to noise erosion as a function of sequence length. In the case of NGS, it may not have the capability to "read" chemically modified nucleotides or identify modified nucleotides as such because of the polymerase functionality and requirements. Inclusion of modified nucleotides is desirable for some oligonucleotide therapeutics and other products.

Another approach uses on-line infrared (IR) analysis in order to identify the sequence during synthesis. However, this technique has the limitation of not being able to easily distinguish differences between modified from unmodified nucleosides. IR spectra comparisons would require in depth visual comparison as the infrared spectral differences between single atom changes such as that in 2'-modified nucleotides is extremely slight. Whereas the distinction between single atom changes for the same 2'-modified nucleotides is a direct measurement molecular mass and even singly mass unit differences is within mass accuracy of the detector.

Accordingly, there is a need for for (in-line) monitoring the synthesis to verify production of verified oligonucleotide sequences. There is also a need for methods and systems for real time monitoring of oligonucleotide synthesis.

SUMMARY

As one aspect of the present invention, a method is provided for synthesizing an oligonucleotide and monitoring the synthesis in real time. The method comprises selecting a nucleotide monomer for addition to an oligonucleotide; feeding an inlet stream to a reaction chamber for oligonucleotide synthesis; provide conditions in the reaction chamber for oligonucleotide synthesis; diverging an outlet stream from the reaction chamber to an analysis station; analyzing the outlet stream or a sample thereof by mass spectrometry (MS) in the analysis station; and determining, based on results from analyzing by MS, whether the outlet stream comprises the selected nucleotide monomer or a derivative thereof.

As another aspect of the present invention, a system for synthesizing an oligonucleotide is provided. The system comprises a reaction chamber comprising an inlet, a solid support for oligonucleotide synthesis, and an outlet; and a mass spectrometry (MS) instrument fluidically connected to the outlet of the reaction chamber.

These and other features and advantages of the present methods and system will be apparent from the following detailed description, in conjunction with the appended claims.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims. Although any methods and materials similar or equivalent to those described herein can also be used in the practice or testing of the present teachings, some exemplary methods and materials are now described.

The present methods and systems can confirm the order of addition of each nucleotide monomer to a growing oligonucleotide in real-time, by using in-line mass spectrometry for analysis of an outlet stream from a reaction chamber of the oligonucleotide synthesizer. The present methods and system solve several problems and provide several advantages. For instance, they provide the first real-time verification during oligonucleotide synthesis and real-time nucleotide monomer addition order by in-line mass spectrometry (MS). They increase the accuracy of sequence verification through assessing the simple individual nucleotide monomer identity that is used in each cycle of the synthesis instead of the entire highly complex final oligonucleotide. The present methods and system are independent of the oligonucleotide length or oligonucleotide chemical modifications. They are also more specific as compared to existing on-line techniques. The present methods and system generally do not require high resolution mass spectrometry.

The present methods and systems can be used to synthesize oligonucleotides such as oligoribonucleotides, oligodeoxyribonucleotides, and chimeric oligonucleotides. The desired oligonucleotide may comprise ribonucleotides, deoxyribonucleotides, or a mixture thereof and modified nucleotides (for example, 2'-O-methyl, 2'-Fluoro, LNA, 2'-MOE, 2'-CNEt, and others). In some embodiments, methods are provided for synthesizing, or monitoring synthesis of, an oligonucleotide of a defined sequence. The methods comprise chemical reagents selected for addition to an oligonucleotide; feeding an inlet stream to a reaction chamber (for example, a column comprising a solid support) for oligonucleotide synthesis; providing conditions in the reaction chamber for oligonucleotide synthesis; diverging an outlet stream from the reaction chamber to an analysis station; utilizing Mass Spectrometry (MS) in the analysis station to analyze the outlet stream at a specified time when it contains the activated nucleotide phosphoramidite solution diverted from the synthesizer post coupling; and determining, based on results from analysis of MS results, whether the outlet stream comprises the selected activated nucleotide monomer or a derivative thereof.

Figure 1:
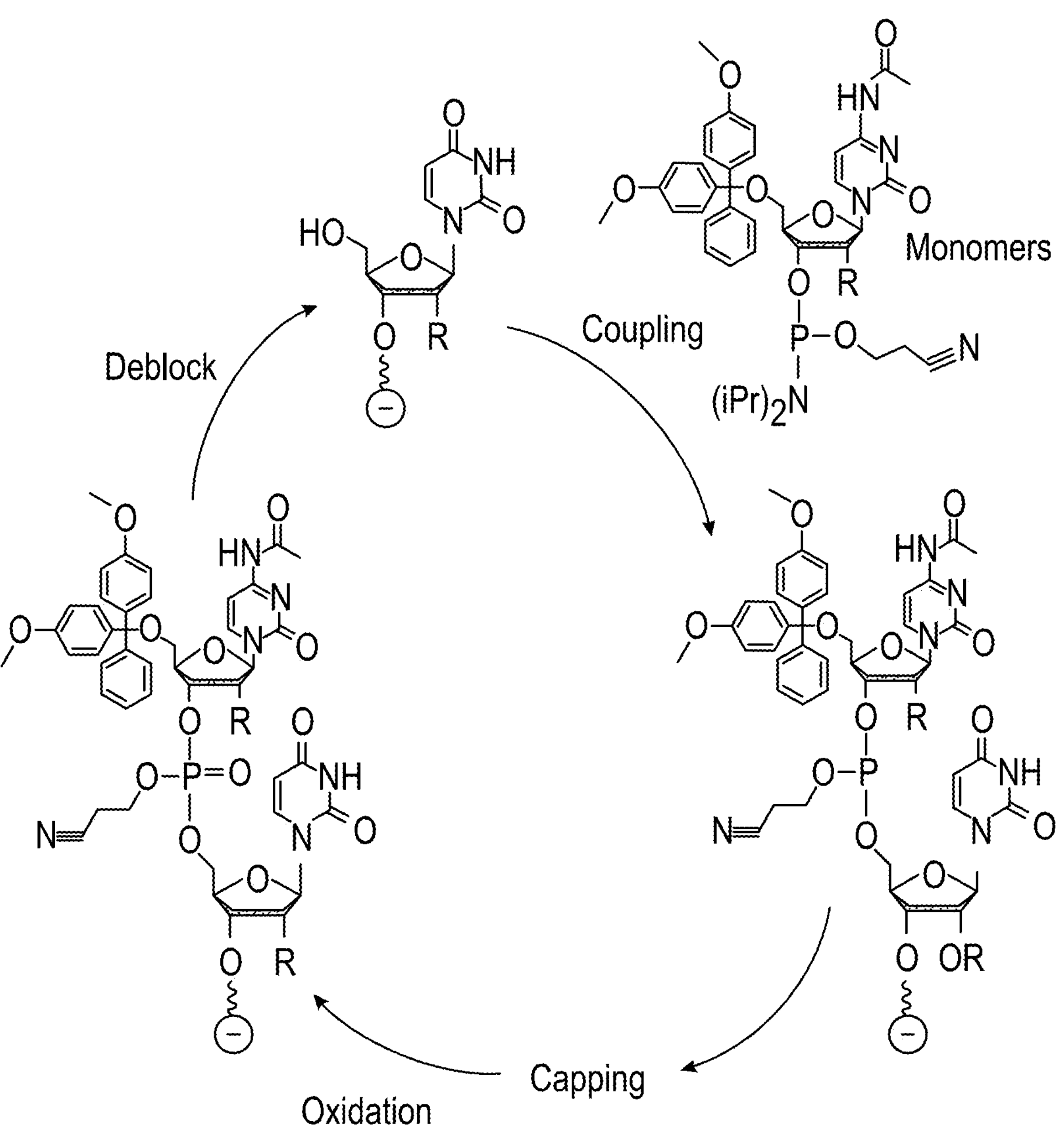
FIG. 1 shows a typical chemical synthesis of an oligonucleotide on a solid support.

FIG. 1 is a schematic of a typical chemical synthesis cycle in the production of an oligonucleotide on a solid support. To accomplish the synthesis, the first step of a synthesis cycle is generally the reaction of a protected nucleotide monomer with a nucleoside attached to the surface of the solid support (beads or resin), or reaction of a protected nucleotide monomer with a hydroxyl group on that surface. The hydroxyl group on the surface can either be part of a cleavable universal linker (such as Unylinker or a succinate linker) or non-cleavable surface attachment. After initial coupling of the reactive phosphorus group with a hydroxyl, the steps that follow typically include capping of unreacted hydroxyl groups and then oxidation of the reactive phosphorus intermediate (phosphite triester to phosphate triester). Typically, oligonucleotides contain an internucleotide bond between the 5'-hydroxyl and 3'-hydroxyl of adjacent nucleotides, which may be a phosphate or a modified phosphorous group (typically a 2-cyanoethyl-protected phosphate group). Under certain conditions where certain modified phosphorus groups are being used, oxidation is performed prior to capping, especially in the case where the oxidation reagent produces a modified phosphorus group such as a phosphorothioate, boranophosphonate, or phosphoramidate. The final step of the synthesis cycle is usually the deblocking of the hydroxyl group of the 5'end of the growing oligonucleotide by removing its protecting group (e.g., dimethoxytrityl group (DMT)). The deblocked hydroxyl group can then be coupled to the next incoming protected nucleotide phosphoramidite monomer fed to the reaction chamber under conditions for coupling reaction. Upon the completion of the coupling of the last nucleotide selected for the sequence, the desired oligonucleotide product is released from the solid phase (resin), deprotected, purified and utilized in further biological applications.

As another aspect of the present disclosure, systems are provided for synthesizing, or monitoring the synthesis of, an oligonucleotide. The systems comprise an automated oligonucleotide synthesizer that includes a reaction chamber comprising at least one inlet by which reagents are provided to the column wherein synthesis of the oligonucleotide is performed, a solid support contained in the column for oligonucleotide synthesis, and an outlet for draining the excess of reagents, solvents and washes to a waste. The systems also comprise a mass spectrometry (MS) instrument fluidically connected to the outlet of the reaction chamber. Suitable reaction chambers for solid phase synthesis of oligonucleotides are described herein as well as in various publications.

Figure 2:
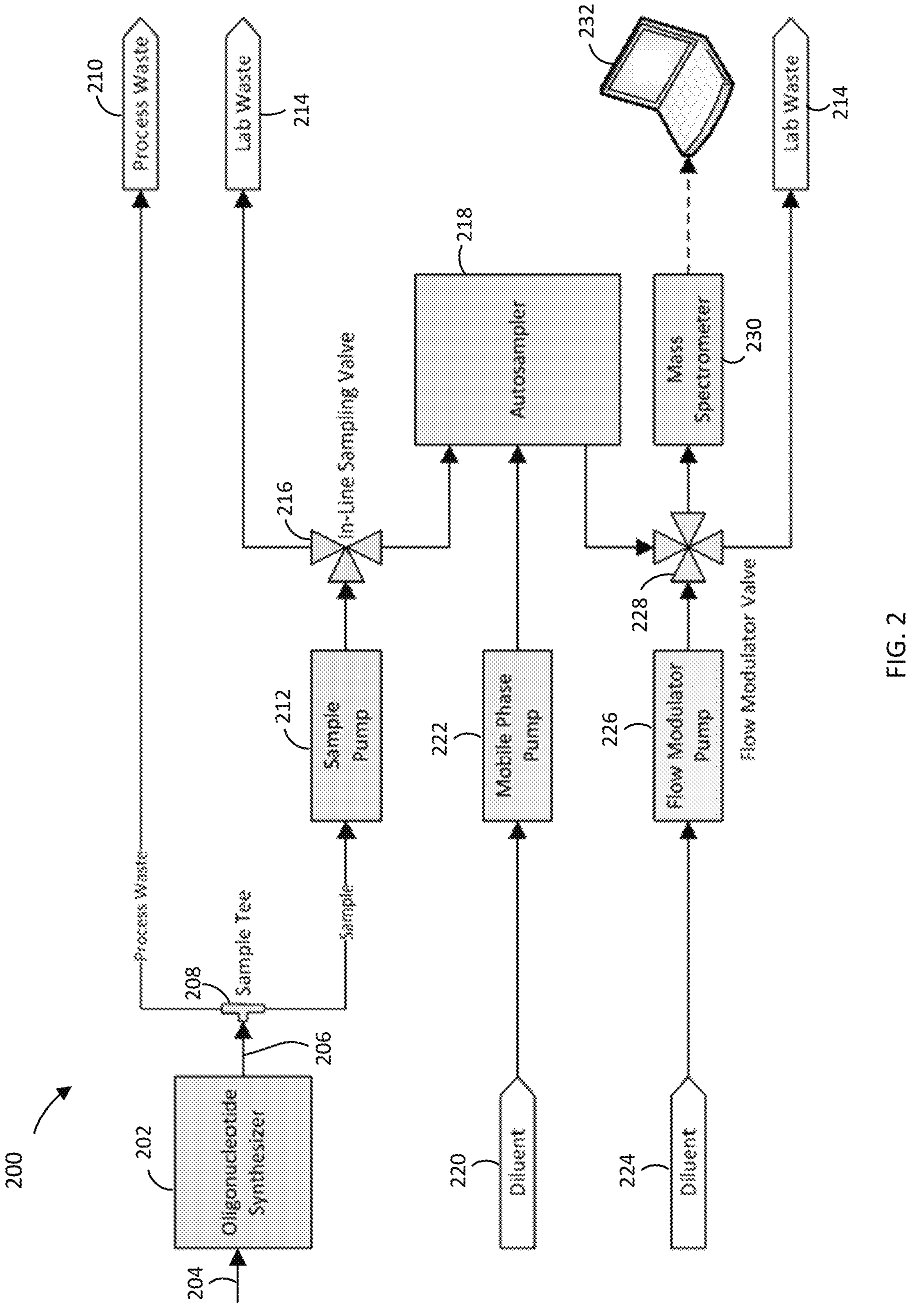
FIG. 2 illustrates an embodiment of the present system.

FIG. 2 illustrates an embodiment of the present system 200. A reaction chamber 202 for oligonucleotide synthesis has an inlet 204 and an outlet 206. The reaction chamber 202 contains a solid support adapted for solid phase synthesis of an oligonucleotide. The reaction chamber 202 may define a column comprising the solid support, such that the components of the inlet stream pass through the column as they move toward the outlet 206. A sample tee 208 receives an outlet stream from the outlet 206, so that the outlet stream can be sent to process waste 210 or for analysis. In some embodiments, some or most of the outlet stream is sent to process waste 210, and a sample of the outlet stream is sent for analysis. A pump 212 provides a native force to flow the outlet stream from the reaction chamber 202 toward the analysis components. For example, an isocratic pump can be used to constantly pump the outlet stream throughout the process. Initially the outlet stream from the 202 reaction chamber will be sent to waste 214, but at a desired time point, such as during a column wash phase of the synthesis, a 'start' signal is sent to execute a series of programmed tasks to automatically collect a sample for retention and analysis. The programmed tasks can include switching a sample valve 216 so that the flow path from an isocratic pump 212 switches flow of the outlet stream from waste 214 to the analytical components, such as by sending the outlet stream, or a sample thereof, to an UHPLC-MS instrument.

A sample is collected from the flowing outlet exit stream using the UHPLC-MS on-line sample manager 218. The collected sample can be placed into a sample vial for analysis and/or retention.

In some embodiments, immediately following creation of the sample, the system 200 will automatically initiate an analytical run of the sample. In some embodiments, the system also comprises a diluent source 220 and mobile phase pump 222 fluidically connected to the on-line sample manager 218. The system can also comprise a MS diluent source 224 and flow modulator pump 226 fluidically connected to the MS instrument 230. A mobile phase pump 222 can control flow of sample from the on-line sample manager 218 to the mass spectrometry instrument 230. During the analysis, the sample can automatically dilute on-line to adjust the concentration of the sample prior to MS detection using the Flow Modulator pump 226 and valve 228. A computing device 232 is communicably connected with the mass spectrometry instrument 230 so that it receives the results of the MS analysis. In certain embodiments, and in particular in large scale manufacturing, if the results show an error on the identity of the expected monomer phosphoramidite, demonstrating that a wrong base was added to the growing oligonucleotide sequence, a automatic shutdown mechanism is put in place to abort the oligonucleotide synthesis.

Figure 3:
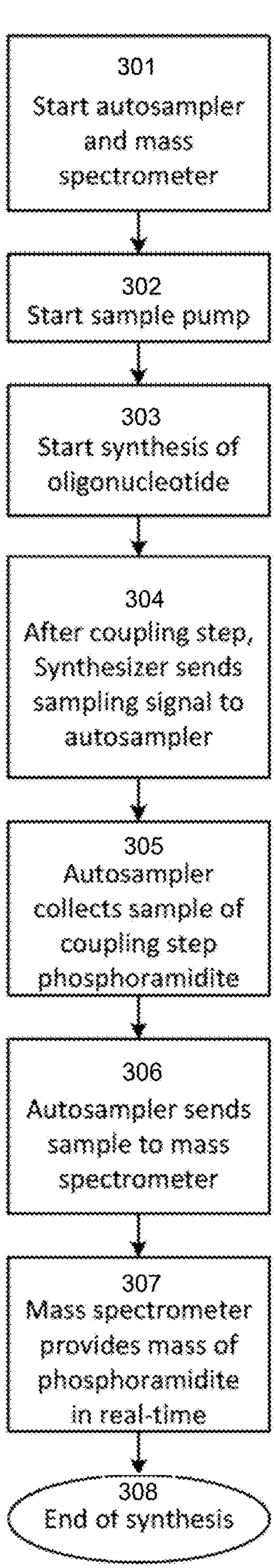
FIG. 3 is a flow diagram for an embodiment of the present method.

FIG. 3 provides a flow chart for an embodiment of the present methods. At 301, the on-line sample manager 218 and mass spectrometer 230 are started. At 302, the sample pump 212 is started. At 303, synthesis of the desired oligonucleotide in the reaction chamber 202 is started. At 304, after a period of conditions for oligo synthesis in the reaction chamber 202 a sampling signal is sent to on-line sample manager 218. The sampling signal can be sent by the reaction chamber 202, by a sensor, or by a computing device communicably connected to the reaction chamber 202 or a sensor associated with the reaction chamber 202. At 305, the on-line sample manager collects sample of outlet stream, including any phosphoramidite. At 306, the on-line sample manager sends sample to mass spectrometer. At 307, the mass spectrometer provides mass of phosphoramidite or derivative thereof in real-time. At 308, when synthesis has ended and the sample collection and analysis are complete, the system can pump idly until another 'start' signal is generated by the reaction chamber 202. This would then initiate the system to start another cycle of sample collection and analysis.

After synthesis completion, the generated sample data is analyzed. Sample/mass identification is assigned. All of the generated sample data is collected by computing device 232 and compiled into a report that confirms the sequence of the oligonucleotide product by confirming the order of nucleotide monomers fed to the reaction chamber. The report can also include timestamps of MS analysis results, feed times of the inlet stream to the reaction chamber, and associations between the timestamples and feed times, residence time, or other data for confirming or verifying.

The present methods and systems can be employed for the synthesis of any desired oligonucleotide product. In some embodiments, the oligonucleotide is an oligoribonucleotide (RNA). In some embodiments, the oligonucleotide is an oligodeoxyribonucleotide (DNA). In some embodiments, the oligonucleotide is a chimeric oligonucleotide, comprising both ribonucleotides and deoxyribonucleotides or modified deoxy/ribo-nucleotides (including but not limited 2'-OMe, 2'F, 2'-MOE, LNA, phosphorothioates, PNA, phosphonate linkages). In some embodiments, the oligonucleotide is at least 15 nucleotides in length. In some embodiments, the oligonucleotide is at least 50 nucleotides in length. In some embodiments, the oligonucleotide is at least 70 nucleotides in length. In some embodiments, the oligonucleotide is at least 75 nucleotides in length. In some embodiments, the oligonucleotide is at least 100 nucleotides in length. In some embodiments, the oligonucleotide is at least 125 nucleotides in length. In some embodiments, the oligonucleotide is at least 150 nucleotides in length. In some embodiments, the oligonucleotide is from about 15 nucleotides to about 500 nucleotides in length. In some embodiments, the oligonucleotide is from about 40 nucleotides to about 300 nucleotides in length.

In some embodiments, the desired oligonucleotide is synthesized using a phosphoramidite-based method. In some embodiments, the synthesis method comprises a support-bound nucleoside having a 5'-DMT protecting group. In some embodiments, the synthesis method comprises a support-bound nucleoside having a 3'-DMT protecting group. In some embodiments, the synthesis method comprises a support-bound nucleoside having a 5'-silyl protecting group. In some embodiments, the synthesis method comprises a support-bound nucleoside having an oxidation removable protecting group. In some embodiments, the synthesis comprises the steps of detritylation, coupling of a support bound nucleoside with a nucleoside phosphoramidite monomer, capping unreacted 5'-hydroxyl groups, and phosphoramidite oxidation. In some embodiments, the oligonucleotide synthesis is automated. In some embodiments, the oligonucleotide is detritylated prior to performing a method of the present invention.

In some embodiments, the oligonucleotide comprises a phosphorus protecting group or a nucleobase protecting group. In some embodiments, the oligonucleotide comprises a phosphorus protecting group and a nucleobase protecting group. In some embodiments, the oligonucleotide is an RNA that comprises a phosphorus protecting group, a nucleobase protecting group, and a 2'-hydroxyl protecting group.

In some embodiments, the selected nucleotide monomer is a ribonucleotide having a 2'-protecting group and a 5'-protecting group. For example, the ribonucleotide may have a 5'-DMT protecting group and a 2'-protecting group selected from the group consisting of a thionocarbamate (TC) protecting group, bis(2-acetoxyethoxy)methyl (ACE) protecting group, t-butyldimethylsilyl (TBDMS) protecting group, triisopropylsilyloxymethyl (TOM) protecting group, pivaloyloxymethyl (PivOM) protecting group and 2-cyanoethoxymethyl (CEM) protecting group.

In some embodiments, the selected nucleotide monomer comprises a phosphorous protecting group, whereby a phosphorus moiety of an oligonucleotide is attached to a phosphorus protecting group. In some embodiments, the phosphorus moiety is a phosphate, phosphoramidite, or a H-phosphonate group. In some embodiments, the phosphorus protecting group is a methyl or cyanoethyl group (e.g., beta-cyanoethyl group). The methyl group may be removed using, for example, thiophenol or disodium 2-carbamoyl-2-cyanoethylene-1,1-dithiolate. The cyanoethyl group may be removed using, for example, a non-nucleophilic or hindered amine such as diethylamine, t-butylamine, or 1,8-Diazabicycloundec-7-ene (DBU).

In some embodiments, the selected nucleotide monomer comprises a nucleobase protecting group. Any nucleobase in the oligonucleotide can comprise a nucleobase protecting group. In some embodiments, the nucleobase protecting group is acetyl, isobutyryl, benzoyl, or the like. For example, the protected-nucleobase may be $N^6$-benzoyl-A, $N^6$-isobutyryl-A, $N^4$-acetyl-C, $N^4$-isobutyryl-C, or $N^2$-isobutyryl-G (include amidine protecting groups such as dimethylacetamidine or the like). In some embodiments, the nucleobase protecting group is removed by contacting the oligonucleotide to a polyamine. In some embodiments, the nucleobase protecting group is removed by contacting the oligonucleotide with a diamine such as 1,2-diaminoethane. In some embodiments, exposing the oligonucleotide to 1,2-diaminoethane for 2 hours at room temperature results in deprotection of the nucleobase. In some embodiments, the nucleobase protecting group is benzoyl, isobutyryl, acetyl, phenoxyacetyl, t-butylphenoxyacetyl, dimethylformamidine, dimethylacetamidine, or the like. In some embodiments, the selected nucleotide monomer comprises a modified nucleobase for example a 5-alkyl-pyrimidine such as 5-methyl-C($m^5C$), 5-hydroxymethyl-C(5hmC), 5-methyl-U ($m^5U$), a $N^6$-alkyl purine such as $N^6$-methyl-A ($m^6A$), a pseudourine (Φ), 1-methylpseudourine ($m^1Φ$), a 2-thiouridine (2sU), a 5-fluoro-U (5FU), 7-deazapurine or any other known modified nucleobases used in oligonucleotide synthesis (see for example Hu, B., Zhong, L., Weng, Y. et al. Therapeutic siRNA: state of the art. *Sig Transduct Target Ther* 5, 101 (2020). https://doi.org/10.1038/s41392-020-0207-x. and Q. Chen, Y. Zhang, H. Yin. Recent advances in chemical modifications of guide RNA, mRNA and donor template for CRISPR-mediated genome editing. *Adv. Drug Deliv. Rev.,* 168 (2021), pp. 246-258.

The synthesis of oligonucleotides can occur in the 3' to 5' direction where the final protective group is removed from the 5'-hydroxyl of the resulting oligonucleotide, or the synthesis can occur in the 5' to 3' direction in which the final protective group is removed from the 3'-hydroxyl of the resulting oligonucleotide.

The synthesized oligonucleotide can be treated with various basic amines (ammonia, ammonium hydroxide, methylamine, ethylenediamine and the like) to optionally remove various protective groups, nucleobase protecting groups and if present, base labile 2'-hydroxyl protecting groups such as TC, or PivOM, and possibly cleave the linker, typically a succinate linker or a unylinker that attaches the oligonucleotide to the solid support.

The 2'-hydroxyl protecting group can be removed using any suitable conditions. In some embodiments, a TC or PivOM protecting group is removed from the 2'-hydroxyl by contacting the oligoribonucleotide with a diamine such as 1,2-diaminoethane. In some embodiments, a PivOM protecting group is removed from the oligoribonucleotide by contacting the oligoribonucleotide with ammonia or an alkyl amine. In some embodiments, contacting the oligoribonucleotide with a diamine, ammonia, or an alkyl amine results in simultaneous deprotection of the 2'-hydroxyl group and cleavage of the oligoribonucleotide from the solid support. In some embodiments, an ACE protecting group is removed by contacting the oligoribonucleotide with an acid.

After coupling of the last nucleotide monomer in the sequence of the desired oligonucleotide product, the synthesized oligonucleotides can be cleaved from the solid support, can be partially (for certain oligoribonucleotides still having 2'-hydroxyl protecting groups) or fully deprotected, then can be eluted from the solid support in a buffer and can exit the reaction chamber through its outlet. A typical buffer can comprise 0.2 M sodium phosphate, 0.6 M sodium chloride, pH 7.4, and 10% dimethylformamide (loading buffer). In some embodiments, the oligonucleotide is treated with 1,2-diaminoethane, thereby removing the 2'-OH protecting group (e.g., TC or PivOM), the nucleobase amine protecting groups (e.g. acetyl, benzoyl, isobutyryl, phenoxyacetyl, amidine) and the phosphorous protecting groups (i.e. beta-cyanoethyl) from the oligonucleotide and cleaving the oligonucleotide from the synthesis solid support simultaneously prior elution.

Nucleotide monomers contain a reactive phosphorus group such as phosphoramidite, H-phosphonate, or other reactive phosphorus or modified groups so that it can be coupled to a hydroxyl group embedded on the solid surface or on the growing oligonucleotide. The nucleotide monomers are derived from protected 2'-deoxynucleosides (dA, dC, dG, and T), protected ribonucleosides (A, C, G, and U), or protected chemically modified nucleosides. The typical desired oligonucleotide product contains an internucleotide bond between the 5'-hydroxyl and 3'-hydroxyl of adjacent nucleotides. However, it may also be desirable to form unnatural internucleotide linkages between any of the hydroxyl groups on adjacent nucleotides.

A "nucleotide" refers to a sub-unit of an oligonucleotide (whether DNA or RNA or analogue thereof) which includes a phosphate group, a sugar group and a heterocyclic base, as well as analogs of such sub-units. Other groups (e.g., protecting groups) can be attached to any component(s) of a nucleotide. A "nucleoside" or "nucleoside moiety" referred to an oligonucleotide subunit including a sugar group and a heterocyclic base, as well as analogs of such sub-units.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases that have been modified. The pyrimidine, purine, heterocyclic base and modified heterocyclic bases are termed herein "nucleobases". Such modifications include methylated purines or pyrimidines, acylated purines or pyrimidines, alkylated heterocycles or other heterocycles. Such modifications include, by way of examples, diaminopurine and its derivatives, inosine and its derivatives, alkylated purines or pyrimidines, acylated purines or pyrimidines, thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, N,N-diphenyl carbamate, or the like. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Modified nucleosides or nucleotides also include modifications on the internucleotide linkage or backbone moiety. "Analogues" refer to molecules having structural features that are recognized in the literature as being mimetics, derivatives, having analogous structures, or other like terms, and include, for example, polynucleotides incorporating non-natural (not usually occurring in nature) nucleotides, unnatural nucleotide mimetics such as 2'-modified nucleosides, peptide oligonucleotides, oligomeric nucleoside phosphonates, and any polynucleotide that has added substituent groups, such as protecting groups or linking groups.

An "oligonucleotide" refers to a compound containing a plurality of nucleoside moiety subunits that are linked by internucleotide linkages. As such, the term also refers to a compound containing a plurality of nucleotide moiety subunits or residues. An oligonucleotide might contain ribonucleosides, or deoxyribonucleosides or a mixture thereof. An oligonucleotide may comprise natural and/or non-natural nucleosides, nucleoside analogs and modified nucleosides and may comprise natural (phosphate diester) and/or non-natural internucleotides linkages (e.g. phosphorothioate, phosphonate, boranophosphonate, phosphoramidate, amido linkage such as peptide nucleic acid (PNA)).

The inlet stream can be fed to the reaction chamber by any suitable technique. Generally, the reaction chamber will have one or more inlets which are connected to sources of reactive nucleotide monomer, other reagents for the coupling and deprotection reactions, and one or more diluents. The inlet stream typically comprises a selected nucleotide monomer which is intended for addition to the oligonucleotide being synthesized. However, it is contemplated that the present methods and systems can reliably and quickly detect if the selected nucleotide monomer is not present in the inlet stream when it is intended to be, possibly due to a mechanical failure or operational error. In some embodiments, the method also comprises stopping the feed of the inlet stream to the reaction chamber if it is determined that the outlet stream does not comprise the selected nucleotide monomer.

In some embodiments, an inlet stream is fed from one or more reservoirs fluidically connected to the inlet of the reaction chamber. The reservoirs can be directly or indirectly connected to the inlet such as via a series of conduits with one or more valves interposed. One of the reservoirs can be a source of the selected nucleotide monomer, and it can be fluidically connected to the inlet stream before the feeding step such as by opening a valve disposed between the reservoir and the inlet. In some embodiments, the step of determining whether the outlet stream comprises the selected nucleotide monomer or a derivative thereof is performed before a subsequent nucleotide monomer is fed to the reaction chamber.

In some embodiments of the methods and system, an oligonucleotide is synthesized in a reaction chamber configured for by solid phase synthesis. In some embodiments, the reaction chamber contains a solid support, for example a planar substrate or a bead. In some embodiments, the solid phase support includes a plurality of discrete resin pieces. In some embodiments, the plurality of discrete resin pieces includes a plurality of resin beads.

In some embodiments, an oligonucleotide is prepared via solid-phase synthesis. In such embodiments, the synthesis is carried out on a solid support held between two filters in columns that enable reagents and solvents to pass through freely. In some embodiments, the synthesis is carried out on a planar surface. In some embodiments, the synthesis is carried out on a non-planar surface. In some embodiments, the synthesis is carried out on a surface of the support where synthesis is occurring is resistant to the diffusion, absorption, or permeation of the relevant reagents and chemicals of oligonucleotide synthesis beyond the surface and into the body of the support (in contrast to some polymeric oligonucleotide reaction chamber supports, which permit such diffusion and permeation, such that oligonucleotide synthesis occurs in the body of the support). In some embodiments, the synthesis is carried out on a substantially smooth surface of the support where the synthesis is occurring is at most superficially irregular, such that irregularities, if any, are not of a scale which would substantially affect the rapidity with which reagents can be uniformly applied to, mixed on, or removed from the surface (in contrast to some controlled pore glass oligonucleotide reaction chamber supports, which contain pores and irregularities that slow the application and removal of reagents). A solid, substantially smooth surface need not be flat, and would include, for example, flat surfaces, tubes, cylinders, arrays of depressions or wells, and combinations of these elements, as well as other designs presenting surface portions with the above-described attributes. For example, substantially smooth surfaces include surfaces (or portions of surfaces) that can be addressed by an inkjet print head.

In some embodiments, an oligonucleotide is attached to a solid support such as a controlled-pore glass, or a polymeric support for example a polystyrene (PS) support. Suitable solid supports are in some cases polymeric and may have a variety of forms and compositions and derive from naturally occurring materials, naturally occurring materials that have been synthetically modified, or synthetic materials. Examples of suitable support materials include, but are not limited to, polysaccharides such as agarose (e.g., that available commercially as Sepharose®, from Pharmacia) and dextran (e.g., those available commercially under the tradenames Sephadex® and Sephacryl®, also from Pharmacia), polyacrylamides, polystyrenes, polyvinyl alcohols, copolymers of hydroxyethyl methacrylate and methyl methacrylate, silicas, teflons, glasses, and the like.

In some embodiments, the synthesis of the oligonucleotide is performed on a solid phase (e.g. CPG) that contains the 3'-terminal nucleotide attached to the solid phase with a base labile linker (such as a succinate linker or Universal Support linker (e.g. Glen Research UnySupport), or a UnyLinker). The synthesis cycle includes deprotection of the 5'-OH protecting group (e.g. trityl or DMT), coupling of a phosphoramidite in the presence of an activator, capping of the unreacted hydroxyl groups with a base labile protecting group (e.g. acetyl protecting group), and oxidation of the phoshitetriester linkage to the phosphatetriester linkage.

The reaction chamber can include or be connected to devices that provide multiple features to accomplish oligonucleotide synthesis, including but not limited to one or more of: delivery of multiple reagents in liquid form from reagent reservoirs to the reaction chamber; delivery of multiple reagents into a vessel which can be used to mix the reagents prior to delivery to the reaction chamber; purging of argon at a steady state flowrate with a needle valve to maintain an inert atmosphere for all reservoirs and the reaction chamber; allowing for delivery of reagents with metering controlled to ensure specified volume of delivery; a mechanism to allow for the resin and solvent inside to agitate and mix; a UV detector that is connected to the outlet to detect the UV absorbance of the outlet stream exiting the reaction chamber; a pressure sensor to detect the pressure in which the reaction chamber is under throughout the synthesis; a pump connecting the solvent reservoirs to the reaction chamber and subsequently to the waste line, to allow for solvents to be fed to the reaction chamber, flow through the reaction chamber, and go directly to waste; a pump that allows for flow from the outlet of the reaction chamber back to the inlet of the reaction chamber, allowing for circulation of the solvent within the reaction chamber; a specific configuration of the pumps and valves, where delivery of the reactive nucleotide monomers to the reaction chamber is through one valve block and pump, and the reagents are delivered through a separate valve block and pump to the reaction chamber, as to prevent cross contamination and ability for cleaning of the valves and line prior to subsequent reagent and monomer delivery.

Along with feeding the inlet stream to the reaction chamber, the present methods comprise providing conditions in the reaction chamber for oligonucleotide synthesis. Such conditions can be established before, during or after the inlet stream is fed to the reaction chamber, such that the conditions are present for at least part of the time when the contents of the inlet stream are in the reaction chamber. Conditions for oligonucleotide synthesis include choice and concentration of nucleotide monomers, choice and concentration of reagents, temperature increases or decreases, etc. In some embodiments, the conditions are adapted or selected to accomplish one or more steps of a method of synthesizing an oligonucleotide. For instance the conditions may result in the method comprising one or more activation steps, one or more coupling steps, one or more capping steps, one or more oxidation steps, one or more detritylation steps, one or more cleavage steps and/or one or more deprotection steps.

In some embodiments, the present methods of synthesis also comprise one or more of the following steps: attaching or coupling a first nucleotide directly to the solid support or indirectly through the 5'-OH of a nucleoside already attached via a linker to the solid support; removing a 5'-protecting group (e.g., DMT) from the first nucleotide; activating the 3'-phosphoramidite of an incoming selected monomer; coupling the selected nucleotide monomer with the 5'-OH of the first nucleotide, whereby the selected nucleotide monomer becomes a second nucleotide—of a growing oligonucleotide—linked by a phosphite triester to the first nucleotide attached to the solid support; oxidizing the phosphite triester to form a phosphate triester; capping any unreacted 5'-OH nucleotides, such as by acetylation.

The present methods and systems can also comprise diverging an outlet stream from the reaction chamber to an analysis station. The timing of outlet stream diverged can be chosen based as the synthesis cycle; generally, the outlet stream will be diverged for analysis prior to or after the expected completion of a cycle. The outlet stream, or a sample of the outlet stream, can then be analyzed by mass spectrometry in an analysis station. If the outlet stream is determined by the MS analysis to contain the selected nucleotide monomer or a derivative thereof, it is thereby confirmed that the selected monomer was indeed fed to the reaction chamber in the proper order and as intended by the defined sequence of the oligonucleotide to be synthesized.

In some embodiments, the MS analysis determines that a derivative of the selected monomer is present in the outlet stream. Derivatives expected in the outlet stream include nucleotide monomers that have lost one or more protecting groups, such as a phosphorous protecting group (for example, a methyl group or a cyanoethyl group) or are present in their activated form (i.e. the diisopropylamine has been replaced with the tetrazole activator or ethylthiotetrazole (ETT)), or the phosphoramidite has been hydrolized to the corresponding H-phosphonate.

In some embodiments, the methods comprise recoding one or more time points related to synthesis of the oligonucleotide, or to the operation of the reaction chamber or its associated devices. For example, a method can include applying timestamps to the results from analyzing by MS, and recording feed times when various inlet streams are fed to the reaction chamber. The method can also comprise associating the timestamps with feed times of the inlet stream, and using the timestamps and associated feed times to determine if the selected nucleotide monomer was present in the inlet stream. In some embodiments, the method comprising using the timestamps and the associate feed times to calculate a nucleotide sequence for the oligonucleotide synthesized in the reaction chamber. In some embodiments, a feed time is recorded for each time when the composition of the inlet stream changes. In some embodiments, a feed time is associated with a timestamp applied to MS analysis results, such as by associating a timestamp with a feed time when they are separated by a selected time interval. The interval can be predetermined, fixed, or variable.

In some embodiments, the one or more timestamps and the one or more feed times are used to determine if the selected nucleotide monomer was present in the inlet stream. In some embodiments, the method also comprises a residence time which corresponds to the measured or estimated time in which a reactant is present in the reaction chamber. The association between the timestamps and the feed times can be based on or correlated to the residence time.

In some embodiments, the synthesis of the desired oligonucleotide is confirmed using the timestamps and the associate feed times to calculate a nucleotide sequence for the oligonucleotide synthesized in the reaction chamber.

In some embodiments, the recorded time points are used as a quality control measure or for verification of the oligonucleotide sequence. In some embodiments, the method further comprises distributing or approving the synthesized oligonucleotide if the calculated nucleotide sequence matches a predetermined nucleotide sequence. In some embodiments, the method further comprises withholding or rejecting the synthesized oligonucleotide if the calculated nucleotide sequence does not match the predetermined nucleotide sequence. In some embodiments, the inlet stream is not analyzed for the selected nucleotide monomer before the feeding step, because the analysis of the outlet stream is sufficient as a quality control measure.

In some embodiments, the present method is a current good manufacturing practice cGMP-compliant production process including appropriate quality controls to produce the desired oligonucleotide product. In some embodiments, the present method is for synthesis of a desired oligonucleotide product suitable for use as an active pharmaceutical ingredient (API), and suitable for clinical use. In some embodiments, the present disclosure provides methods and systems for controlling the quality of oligonucleotides produced in solid phase synthesis, wherein the method is included a cGMP compliant production process.

In some embodiments, the present methods further comprise comparing the results of the MS analysis of the outlet stream or a sample thereof to one or more predetermined MS patterns. In some embodiments, the MS analysis comprises assessing the spectrometric results for fragments having masses of 250-1000 Da. For example, when the selected nucleotide monomer is 793.3 and the outlet stream is determined to comprise the selected nucleotide monomer if the MS detects a fragment having a mass of 792.3-794.3 Da.

In some embodiments, the method further comprises one or more steps for purifying an oligonucleotide. By way of example, the method can comprise synthesizing an oligonucleotide on a solid support; reacting the oligonucleotide with an orthoester linker to form an oligonucleotide-orthoester linker conjugate, wherein the orthoester linker comprises an affinity tag; cleaving the oligonucleotide-orthoester linker conjugate from the solid support used for synthesis; isolating the oligonucleotide-orthoester linker conjugate using a chromatographic or affinity capture method; and cleaving the orthoester linker from the oligonucleotide orthoester linker conjugate, thereby releasing a purified oligonucleotide. Further details and teachings regarding purification of oligonucleotides can be found in Dellinger et al. US Pat. App. Pub. 2020/0181124 A1.

The present methods and systems also employ or include a mass spectrometry (MS) instrument. The MS instrument may generally include an ion detector, a mass analyzer, and a detector.

The mass analyzer may be any device configured for separating, sorting or filtering analyte ions on the basis of their respective masses (e.g., mass-to-charge ratios, or m/z ratios). Examples of mass analyzers include, but are not limited to, multipole electrode structures (e.g., mass filters, ion traps), time-of-flight (TOF) analyzers, electrostatic analyzers (ESAs), and magnetic sectors. The mass analyzer may include a system of more than one mass analyzer, particularly when ion fragmentation is desired. As examples, the mass analyzer may be a tandem MS or $MS^n$ system. As another example, the mass analyzer may include a mass filter followed by a collision cell or other ion fragmentation device, which in turn is followed by another mass filter or analyzer.

The MS instrument comprises a detector configured for analyzing a sample by measuring the mass-to-charge ratio of ions received by the detector. The result may be presented as a mass spectrum, a plot of intensity as a function of the mass-to-charge ratio. Mass spectrometry is useful for distinguishing components of complex mixtures. In some embodiments, the MS instrument is selected from the group consisting of a time-of-flight mass spectrometer, a single quadrupole (SQ) LC/MSD, a triple quadrupole (TQ) LC/MS and a quadrupole time of flight (TOF/Q-TOF).

In some embodiments, the MS analysis is performed with a low-resolution detector. The instruments can be configured for direct injection mass spectrometry, liquid chromatography/mass spectrometry, gas chromatography/mass spectrometry, ion mobility/mass spectrometry, supercritical fluid chromatography/mass spectrometry, or any combination thereof. In some embodiments, the outlet stream is analyzed by liquid chromatography/mass spectrometry (LC/MS), or by ultra-high pressure liquid chromatography (UHPLC). In some embodiments, the MS instrument is a low-resolution MS instrument. As used herein, "low resolution" refers to mass spectrometry analysis that gives mass-to-charge ratio of two decimal digits.

In some embodiments, the outlet stream or a sample thereof is purified using high performance liquid chromatography (HPLC) prior to analysis by mass spectrometry. The outlet stream is generally introduced into the HPLC as a mixture comprising a plurality of components. In some embodiments, the present method allows for separation of a nucleotide monomer from other components of the outlet stream which may be of a similar size. The other component(s) may be of any type. In some embodiments, the outlet stream or a sample thereof is purified using reverse-phase HPLC, such as by using a reverse-phase column (e.g., C5 or C18 hydrocarbon column). In some embodiments, the outlet stream or sample thereof is purified on a normal-phase HPLC column. The HPLC system may comprise an injector, pump, and an HPLC column. In some embodiments, the HPLC system is connected to a triple quadrupole LC-MS, Orbitrap LC-MS, Ion Trap LC-MS, or TOF LC-MS. In some embodiments, the present methods and system include an Ultra High-Pressure Liquid Chromatograph Mass Spectrometer (UHPLC-MS) fluidically connected to a reaction chamber.

In some embodiments, the present system also includes an on-line sample manager between the outlet of the reaction chamber and the MS instrument. The on-line sample manager receives the outlet stream from the reaction chamber and delivers the outlet stream or a sample thereof to the MS instrument. The system can also include one or more pumps between the reaction chamber and the on-line sample manager. The system can also include one or more valves between the on-line sample manager and the MS instrument.

Other components of the present systems can include one or more computing devices connected to the reaction chamber and/or its associated components. One or more computing devices connected to the MS instrument; it may be the same computing device connected to the reaction chamber, or it may be a separate independent computing device. For instance, the present can include one or more computing devices communicably connected with the reaction chamber, the on-line sample manager, and/or the MS instrument, wherein the one or more computing devices comprises a processor and a storage medium. The processor is configured to execute instructions stored on the storage medium to determine, based on data from the MS instrument, whether an outlet stream from the reaction chamber comprises a selected nucleotide monomer or a derivative thereof. The one or more computing devices is can also be configured to create, maintain, adjust or otherwise control conditions within the reaction chamber; and/or start and/or stop the feeding of an inlet stream to the reaction chamber; and/or activate and/or deactivate the on-line sample manager. In some embodiments, the instructions stored on a computer medium include instructions for various laboratory functions and/or instrument operations, such as for operation of a liquid chromatography device. Such instructions may be integrated with, or separate from, instructions for operation of the reaction chamber and/or the MS instrument.

In some embodiments, the system also comprises a sensor at the outlet of the reaction chamber, wherein the sensor detects presence or absence of nucleotide monomer in a diluent, or the presence or absence of other components of the inlet stream. The sensor can be communicably connected with the one or more computing devices, and the one or more computing devices can also be configured to direct the outlet stream to the on-line sample manager and/or to activate the on-line sample manager, if the sensor detects the presence of a nucleotide monomer in the outlet stream, or the presence or absence of another component.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

It is to be understood that the terminology used herein is for purposes of describing particular embodiments only and is not intended to be limiting. The defined terms are in addition to the technical and scientific meanings of the defined terms as commonly understood and accepted in the technical field of the present teachings.

The term "valve" generally encompasses any structure that can be adjusted (such as by switching or turning on or off) to change a flow path into, out of, and/or through the structure. Generally, a valve is substantially fluid-tight so as to prevent loss of fluid from the flow path. An example of a suitable valve (e.g., the first, second, third, or fourth valve) is a rotary valve, such as a rotary valve comprising a stator and a rotor. A rotary valve comprises a stator and a rotor, wherein one or both of the stator and the rotor are rotable to different rotary valve positions. The stator and the rotor have surfaces adjacent to each other, and one or both is configured to rotate with respect to the other. The valve inlets and outlet(s) in this embodiment are passages or through-holes in the stator. The rotor comprises a switchable fluid path, which may be a groove in the rotor surface. By rotating the stator and/or the rotor, the fluid path connects a different valve inlet with the valve outlet. Other examples of suitable valves are diaphragm valves. Typical valve materials include metal materials which may or may not be inert. The valve desirably has low dead-volume so as to leave a low flush time and not trap sample.

The term "conduit" generally encompasses any structure configured to define a flow path for fluid to travel from one point (e.g., an inlet of the conduit) to another point (e.g., an outlet of the conduit), though a conduit can deliver fluid to intermediate points as well. A conduit can be flexible, rigid, or both in some measure or portions. A conduit can be relatively long or short, and/or linear or nonlinear, so long as it provides a flow path from one component (such as a gas source) to another component (such as a vent). For example, a conduit can be a long tube, a short fitting, or a manifold with multiple entrances and/or exits. A conduit typically has an entrance and an exit, though in some embodiments, a conduit can have multiple entrances and/or exits, such as where a conduit with two or more entrances converges or joins to one exit, or where a conduit with one entrance diverges or splits to two or more exits. A conduit is often described by its length and inner diameter (i.d.) which can be used to calculate a volume of a conduit. The geometry of a conduit may vary widely and includes circular, rectangular, square, D-shaped, trapezoidal or other polygonal cross-sections. A conduit may comprise varying geometries (e.g., rectangular cross-section at one section and trapezoidal cross-section at another section).

The term "connected" means that two components are fluidically connected, physically connected, and/or communicably connected. The term "fluidically connected" means that two components are in fluid communication and includes direct connections between the two components as well as indirect connections where one or more other components are in the flow path between the two components. For example, a first component and a second component are fluidically connected if an outlet from the first component is physically connected to an inlet of the second component, or if a conduit connects the first and second components, or if one or more intervening components, such as a valve, a pump, or other structure, is between the two components as fluid flows from the first component to the second component, or vice versa. Components can be physically connected in any suitable way, such as by using ferrules, brazing, and other approaches. In general, physical connections that are fluid-tight and/or that minimize dead-volume are desired for the present apparatus. The term "communicably connected" means that two components are able to exchange information, such as by transmitting and receiving communication data. Components can be communicably connected through a wired communication network or a wireless communication network. A wired network generally comprises a circuit for wired communication and conforms to a known communication standard such as Ethernet, and performs a process of transmitting and receiving communication data to and from an external computing device via a network such as the Internet. A wireless network (such as WiFi) generally comprises communication by radio or other waves, and may be through antenna. Wireless communication generally conforms to known communication standards such as IEEE 802.11, to perform a process for transmitting and receiving communication data transmitted and received to and from an external component.

The term "linker" as used herein refers to a hydrocarbyl chain (e.g., (C1-C12)alkylene, (C2-C12)alkenylene, (C2-C12)alkynylene), optionally substituted with a substituent group, or interspersed with other atoms, as represented by —(CHR')a-Wb-(CHR')c-Vd-(CHR')e-, wherein W and V are independently —O—, —S—, or —NR'—; R' is H or (C1-C6)alkyl; and a, b, c, d, and e are independently an integer from 0 to 10, preferably from 0 to 6, or preferably from 0 to 3, and the sum of a, b, c, d, and e is preferably an integer from 2 to 6. The hydrocarbyl chain may be interspersed with —O—R", —O—CO—R", —NR'—R", —NR'—CO—R", —CO—NR'—R", —CO—R", or a combination thereof, wherein R' and R" are independently H or (C1-C6)hydrocarbyl.

A "thionocarbamate protecting group" refers to a protecting group that includes a thionocarbonyl with a nitrogen and an oxygen bonded to the thionocarbonyl carbon atom: —O—C(S)N—.

The term "electron withdrawing group" refers to a chemical group that draws electrons away from a reaction center. Nonlimiting examples of electron withdrawing groups (EWG) are halogens (e.g., fluorine and chlorine), haloalkyls (e.g. CH2Cl, CF3 and the like), nitriles (—RCN), carbonyls (—COR), sulfonyls (—SO3R), ammonium (N+R3) and nitro groups (—NO2).

The term "chromatographic method" refers to a method of separating one or more compounds involving the use of a stationary phase and a mobile phase or eluent that moves through or across the stationary phase. Non-limiting examples of chromatographic methods include fluorous affinity purification, high performance liquid chromatography, and gas chromatography.

The term "alkyl" refers to a straight-chain or branched alkyl, preferably having 1, 2, 3, 4, 5, 6, 7, 8, 9, 10, 11, 12, 13, 14, 15, 16, 17, 18, 19, 20, 21, 22, 23 or 24 carbons. Examples of such alkyl groups include methyl, ethyl, propyl, isopropyl, n-butyl, sec-butyl, isobutyl, tert-butyl, pentyl, isoamyl, hexyl, and the like. In some embodiments, an alkyl group may be a cycloalkyl group.

Alkyl groups may be unsubstituted or substituted, as defined above. The term "halosubstituted alkyl" refers to an alkyl group substituted with one or more halogen atoms. Nonlimiting examples include trifluoromethyl, trifluoroethyl, pentafluoroethyl, 2,2,2-trichloroethyl, chloromethyl, and the like. Halosubstituted alkyl groups may be unsubstituted or substituted, as defined above. The term "fluorosubstituted alkyl" refers to an alkyl group substituted with one or more fluorine atoms.

The term "alkenyl" refers to a straight or branched hydrocarbon, preferably having 2, 3, 4, 5, 6, 7, 8, 9, 10, 11, 12, 13, 14, 15, 16, 17, 18, 19, 20, 21, 22, 23 or 24 carbons, and having one or more carbon-carbon double bonds. Nonlimiting examples of alkenyl groups include ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above. The term "halosubstituted alkenyl" refers to an alkenyl group substituted with one or more halogen atoms. The term "fluorosubstituted alkenyl" refers to an alkenyl group substituted with one or more fluorine atoms.

The term "alkynyl" refers to a straight or branched hydrocarbon, preferably having 2, 3, 4, 5, 6, 7, 8, 9, 10, 11, 12, 13, 14, 15, 16, 17, 18, 19, 20, 21, 22, 23 or 24 carbons, and having one or more carbon-carbon triple bonds. Alkynyl groups include, but are not limited to, ethynyl, propynyl, and butynyl. Alkynyl groups may be unsubstituted or substituted by one or more suitable substituents, as defined above. The term "halosubstituted alkynyl" refers to an alkynyl group substituted with one or more halogen atoms. The term "fluorosubstituted alkynyl" refers to an alkynyl group substituted with one or more fluorine atoms.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo-carbocycles includes naphthyl.

"Heteroalkyl", "heteroalkenyl" and "heteroalkynyl" refers respectively to an alkyl group, an alkenyl group and an alkynyl group, in which one or more carbon atoms have been replaced with a heteroatom, such as, O, N, or S. Any carbons within the alkyl group, the alkenyl group or the alkynyl group can be replaced independently with a heteroatom (O, N, or S), meaning the first carbon, the terminal carbon or an internal carbon. For example, if the carbon atom of an alkyl group which is attached to the parent molecule is replaced with a heteroatom (e.g., O, N, or S) the resulting heteroalkyl groups are, respectively, an alkoxy group (e.g., $—OCH_3$, etc.), an amine alkyl (e.g., $—NHCH_3$, $—N(CH_3)_2$, etc.), or a thioalkyl group (e.g., $—SCH_3$). If a non-terminal carbon atom of the alkyl group which is not attached to the parent molecule is replaced with a heteroatom (e.g., O, N, or S) the resulting heteroalkyl groups are, respectively, an alkyl ether (e.g., $—CH_2CH_2—O—CH_3$, etc.), an alkyl amine (e.g., $—CH_2NHCH_3$, $—CH_2N(CH_3)_2$, etc.), or a thioalkyl ether (e.g., $—CH_2—S—CH_3$). If a terminal carbon atom of the alkyl group is replaced with a heteroatom (e.g., O, N, or S), the resulting heteroalkyl groups are, respectively, a hydroxyalkyl group (e.g., $—CH_2CH_2—OH$), an aminoalkyl group (e.g., $—CH_2NH_2$), or an alkyl thiol group (e.g., $—CH_2CH_2—SH$). A heteroalkyl group, a heteroalkenyl group, or an heteroalkynyl group can have, for example, 1 to 24 carbon atoms. A $C_1$-$C_6$ heteroalkyl group means a heteroalkyl group having 1 to 6 carbon atoms. A "substituted heteroalkyl", a "substituted heteroalkenyl", or a "substituted heteroalkynyl" means a heteroalkyl, a heteroalkenyl or a heteroalkynyl as defined herein in which one or more hydrogen atom has been replaced with a non-hydrogen substituent as defined in the "substituted" definition.

The term "aryl" refers to an unsubstituted or substituted aromatic carbocyclic substituent, as commonly understood in the art, having 3 to 7 carbon atoms as a monocycle, 7 to 12 carbon atoms as a bicycle, and up to about 20 carbon atoms as polycycle such as phenyl, naphthyl, anthracyl, indanyl, and the like. It is understood that the term aryl applies to cyclic substituents that are planar and comprise 4n+2 electrons, according to Hückel's Rule. Aryl groups may be unsubstituted or substituted by one or more suitable substituents, as defined above. The term "halosubstituted aryl" refer to aryl substituted with one or more halogen atoms or halogen-containing substituents. The term "fluorosubstituted aryl" refer to aryl substituted with one or more fluorine atoms or fluorine-containing substituents.

"Arylalkyl" refers to an acyclic alkyl group in which one of the hydrogen atoms bonded to a carbon atom, typically a terminal carbon atom, is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 24 carbon atoms, e.g., the alkyl carbon atoms and the aryl carbon atoms add up to 6 to 24 carbon atoms. Aryl groups may be unsubstituted or substituted by one or more suitable substituents, as defined above.

The term "carbonyl" refers to a substituent comprising a carbon double bonded to an oxygen. Examples of such substituents include aldehydes, ketones, carboxylic acids, esters, amides, carbonates, and carbamates. Carbonyl groups may be unsubstituted or substituted by one or more suitable substituents, as defined above.

The term "amino" refers to any nitrogen-containing moiety. Non-limiting examples of the amino group are $NH_2—$ (primary), RHN— (secondary), and $R_2N$ (tertiary) where R is alkyl, alkenyl, alkynyl, aryl, heterocyclic, or heteroaryl. RHN— and $R_2N$ groups may be unsubstituted or substituted, as defined above.

The term "heteroaryl" refers to a monocyclic or bicyclic 5- or 6-membered ring system, wherein the heteroaryl group is unsaturated and satisfies Hückel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like. Heteroaryl groups may be unsubstituted or substituted, as defined above.

The term "heterocycle" or "heterocyclyl" refers to a monocyclic, bicyclic, or tricyclic moiety containing 1 to 4 heteroatoms selected from O, N, and S. Heterocyclyl groups optionally contain one or more double bonds. Heterocyclyl groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Nonlimiting examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, as defined above.

"Halogen" or "halo" refers to fluorine, chlorine, bromine, and iodine.

As used in the specification and appended claims, and in addition to their ordinary meanings, the terms "substantial" or "substantially" mean to within acceptable limits or degree to one having ordinary skill in the art. For example, "substantially cancelled" means that one skilled in the art considers the cancellation to be acceptable.

As used in the specification and the appended claims and in addition to its ordinary meaning, the terms "approximately" and "about" mean to within an acceptable limit or amount to one having ordinary skill in the art. The term "about" generally refers to plus or minus 15% of the indicated number. For example, "about 10" may indicate a range of 8.5 to 11.5. For example, "approximately the same" means that one of ordinary skill in the art considers the items being compared to be the same.

In the present disclosure, numeric ranges are inclusive of the numbers defining the range. It should be recognized that chemical structures and formula may be elongated or enlarged for illustrative purposes.

Whenever a range of the number of atoms in a structure is indicated (e.g., a $C_1$-$C_{24}$ alkyl, $C_2$-$C_{24}$ alkenyl, $C_2$-$C_{24}$ alkynyl, etc.), it is specifically contemplated that the substituent can be described by any of the carbon atoms in the sub-range or by any individual number of carbon atoms falling within the indicated range. By way of example, a description of the group such as an alkyl group using the recitation of a range of 1-24 carbon atoms (e.g., $C_1$-$C_{24}$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-24 carbon atoms (e.g., $C_2$-$C_{24}$) encompasses and specifically describes an alkyl group having any of 1, 2, 3, 4, 5, 6, 7, 8, 9, 10, 11, 12, 13, 14, 15, 16, 17, 18, 19, 20, 21, 22, 23 and 24 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 1-13 carbon atoms, 1-14 carbon atoms, 1-15 carbon atoms, 1-24 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 2-13 carbon atoms, 2-14 carbon atoms, 2-15 carbon atoms, 2-16 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 3-13 carbon atoms, 3-14 carbon atoms 3-15 carbon atoms, 3-16 carbon atoms, 3-17 carbon atoms, 3-18 carbon atoms, 3-19 carbon atoms, 3-20 carbon atoms, 3-21 carbon atoms, 3-22 carbon atoms, 3-23 carbon atoms and/or 3-24 carbon atoms, as appropriate).

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

All patents and patent publications referred to herein are expressly incorporated by reference.

As used in the specification and appended claims, the terms "a," "an," and "the" include both singular and plural referents, unless the context clearly dictates otherwise. Thus, for example, "a device" includes one device and plural devices.

Unless defined otherwise, all technical and scientific terms used herein have the same meaning as commonly understood by those working in the fields to which this disclosure pertain.

EXAMPLES

General Methods

DNA and RNA strands are chemically synthesized by conjugating each nucleotide sequentially. At each nucleotide addition, a portion of the nucleotide solution is diverted from the column outlet of the synthesizer to an on-line sample manager or other comparable sample preparation and injection apparatus with mass spectrometer equipped. Sample concentration and/or ionic strength adjustment is performed by programming the on-line sample manager to automatically dilute pre- or post-sample injection. This results in a real time sample aliquot ready for use in identity testing. The sample is then automatically prepared and injected into a Mass Spectrometry Detector (MSD) for mass identification.

Synthesis was performed with an AKTA Oligopilot with positions for delivery of multiple different amidite solutions. The synthesis support was loaded into a 2 cm×2.54 cm synthesis column to provide a reaction chamber for oligonucleotide synthesis. The amidites were each prepared at a concentration of 200 mM in ACN.

A sample stream is continuously withdrawn from the outlet of the reaction chamber for the purpose of analysis by mass spectroscopy for determining the identity of amidites and verification of the order in which the amidites were added.

A sample tee on the reaction chamber located downstream from the outlet splits the outlet stream with one branch of the tee directed to process waste and the other directed to a sample pump, and then to a sample valve on the on-line sample manager. The sample tee is located close to the outlet from the reaction chamber to minimize longitudinal back-mixing.

The sample pump installed between the sample branch of the tee and the mass spectrometer provides a continuous and steady sample stream to the mass spectrometer for the duration of the synthesis. The sample pump is located near the sample tee to minimize the length of tubing between the sample tee and pump and maintain adequate priming pressure for reliable pump function. The pump moves sample through post pump tubing (lengths up to 30 meters were evaluated) of narrow bore tubing across the laboratory to the mass spectrometer. Narrow bore tubing between the pump and mass spectrometer is used to preserve the integrity of the sample by minimizing the hold-up volume within the tubing which minimizes back-mixing caused by longitudinal diffusion over long distances.

The sample valve on the on-line sample manager normally directs the stream from the pump to sample waste located at the on-line sample manager. Upon receipt of an electrical signal from the reaction chamber, the sample valve diverts the sample stream for collection of a sample. Signaling is controlled by specific commands inserted into the reaction chamber method code. The flow rate of the sample pump is used to adjust the arrival time of the intended sample to coincide with the sample signal from the reaction chamber. Collected samples may be immediately analyzed or subsequently analyzed by mass spectrometry.

By providing a steady and continuous sample stream from a point at the outlet of the reaction chamber, samples may be collected at any time for verification of the identity of the outlet stream from steps other than coupling.

Example 1

In this example, the nucleotide sequence was confirmed for an oligonucleotide containing eight nucleotides, including modified nucleotides. An 8-base ribonucleic acid (RNA) oligonucleotide sequence consisting of both 2'-fluoro and 2'-methoxy RNA nucleotides was synthesized with the NCEV system connected to the reaction chamber. A standard nucleic acid solid-phase synthesis regimen of 1) detritylation, 2) coupling, 3) oxidation and 4) capping. The solid-support used CPG and was preloaded with 3'-DMT-5' dT.

Synthesis reagents utilized are in Table 1. All washing steps are performed with acetonitrile.

TABLE 1

| Summary of Inputs for Synthesis Steps | |
|---|---|
| Step | Input |
| Detritylation | 10% DCA in toluene |
| Coupling | Standard 2'F or 2'OMe, 5'-DMT, N-base protected, b-cyanoethyl phosphoramidites in acetonitrile and ETT in acetonitrile. A is protected with benzoyl (bz), Gis protected with isobutyryl (iBu), and Cis protected with acetyl (Ac). |
| Oxidation | iodine, $H_2O$, pyridine |
| Capping | Cap NMI and Cap Ala |

The reaction chamber setup was the same as listed under the General Method Information section.

Sample creation and analysis was performed using a customized Agilent 1290 UHPLC consisting of two (2) analytical pumps (Sample and Mobile Phase), an On-line sample manager (AS) with an external valve and custom rotor seals, and an Agilent 6135XT single quadrupole MSD. The samples were automatically diluted with Acetonitrile (ACN) at the time of sample collection (pre-sample injection) using the AS. The Mobile Phase Pump solution was 0.1% Formic Acid+50% ACN. The instrument parameters utilized are listed in Table 2.

TABLE 2

| UHPLC-MS method parameters | |
|---|---|
| **HPLC Parameters** | |
| Sample Pump Flow Rate | 3.0 mL/min |
| Mobile Phase Pump Flow Rate | 0.2 mL/min |
| Injection Volume | 2.0 μL |
| Dilution Factor | 5 x |
| Stop time | 1 min |
| **Single Quadrupole MSD Parameters** | |
| Ionization Mode | ESI |
| Polarity | Positive |
| Drying Gas Temperature | 300° C. |
| Drying Gas Flow Rate | 11 L/min |
| Nebulizer | 28 psig |
| Capillary Voltage | 3500 V |
| Mass Range | 100-2000 m/z |
| Dwell Time | 800 ms |
| Fragmentor | 10 V |
| Gain | 1 |

Nucleotides were conjugated in the following order: 3'-fAfAmCfCmGfAfGmA-5'. Each nucleotide addition was collected and analyzed. The experimental data is shown in Table 3 and FIGS. 4 to 11. The chemical species detected is the product of water quenching the activated amidite and forming the H-phosphonate species (Scheme 1). Water is added to synthesis matrix in preparation of the sample for mass spectroscopy measurement.

Scheme 1 illustrates phosphoramidite quench species formation:

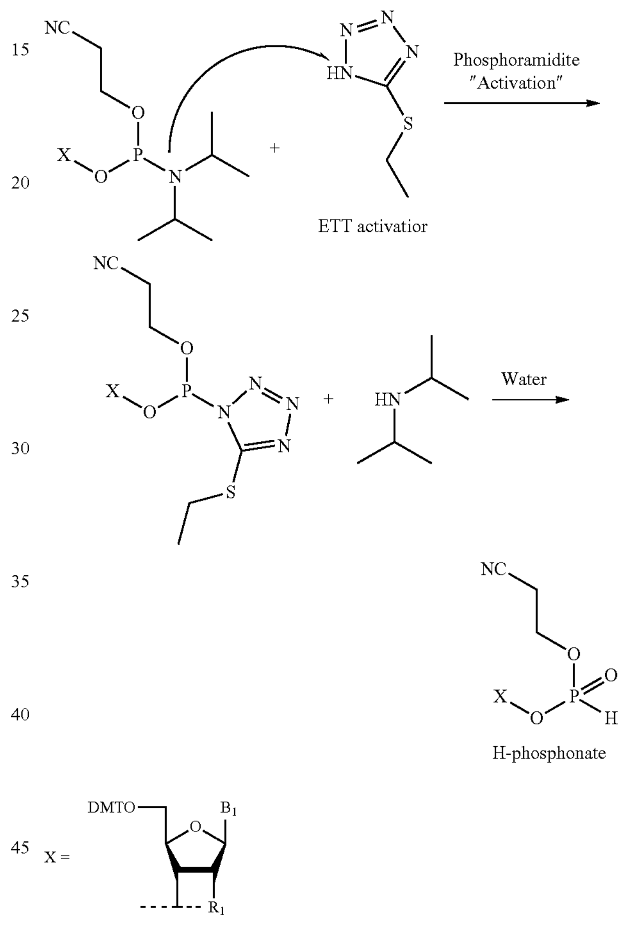

TABLE 3

| Experimental Data from Example 1 | | | | | | |
|---|---|---|---|---|---|---|
| Sample Number | Mass Observed | Theoretical Positive mode Free Acid mass (+1H) | Absolute Difference from Theoretical Positive Mode Mass | Proposed Species by Mass | Actual Species | Confirmed? |
| 1-1 | 793.4 | 793.3 | 0.1 | fA | fA | Yes |
| 1-2 | 793.4 | 793.3 | 0.1 | fA | fA | Yes |
| 1-3 | 719.4 | 719.7 | 0.3 | mC | mC | Yes |
| 1-4 | 707.3 | 707.2 | 0.1 | fC | fC | Yes |
| 1-5 | 787.4 | 787.3 | 0.1 | mG | mG | Yes |
| 1-6 | 793.4 | 793.3 | 0.1 | fA | fA | Yes |
| 1-7 | 775.4 | 775.3 | 0.1 | fG | fG | Yes |
| 1-8 | 805.4 | 805.3 | 0.1 | mA | mA | Yes |

Figure 4:
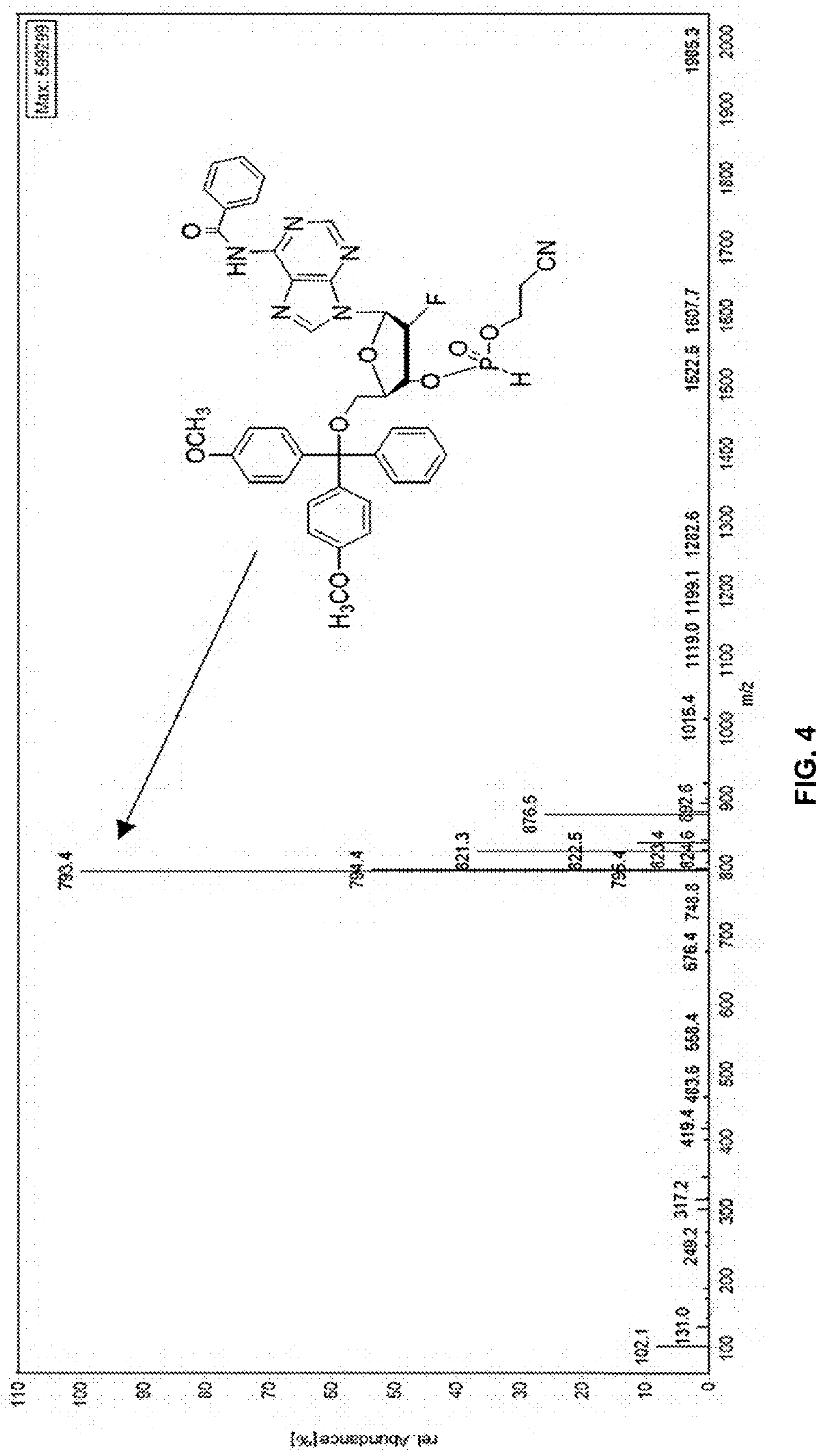
FIGS. 4 to 11 show mass spectral data from Samples 1-1 to 1-8, respectively, from Example 1.

FIG. 4 shows mass spectral data from Sample 1-1 with theoretical chemical structure (fA).

Figure 5:
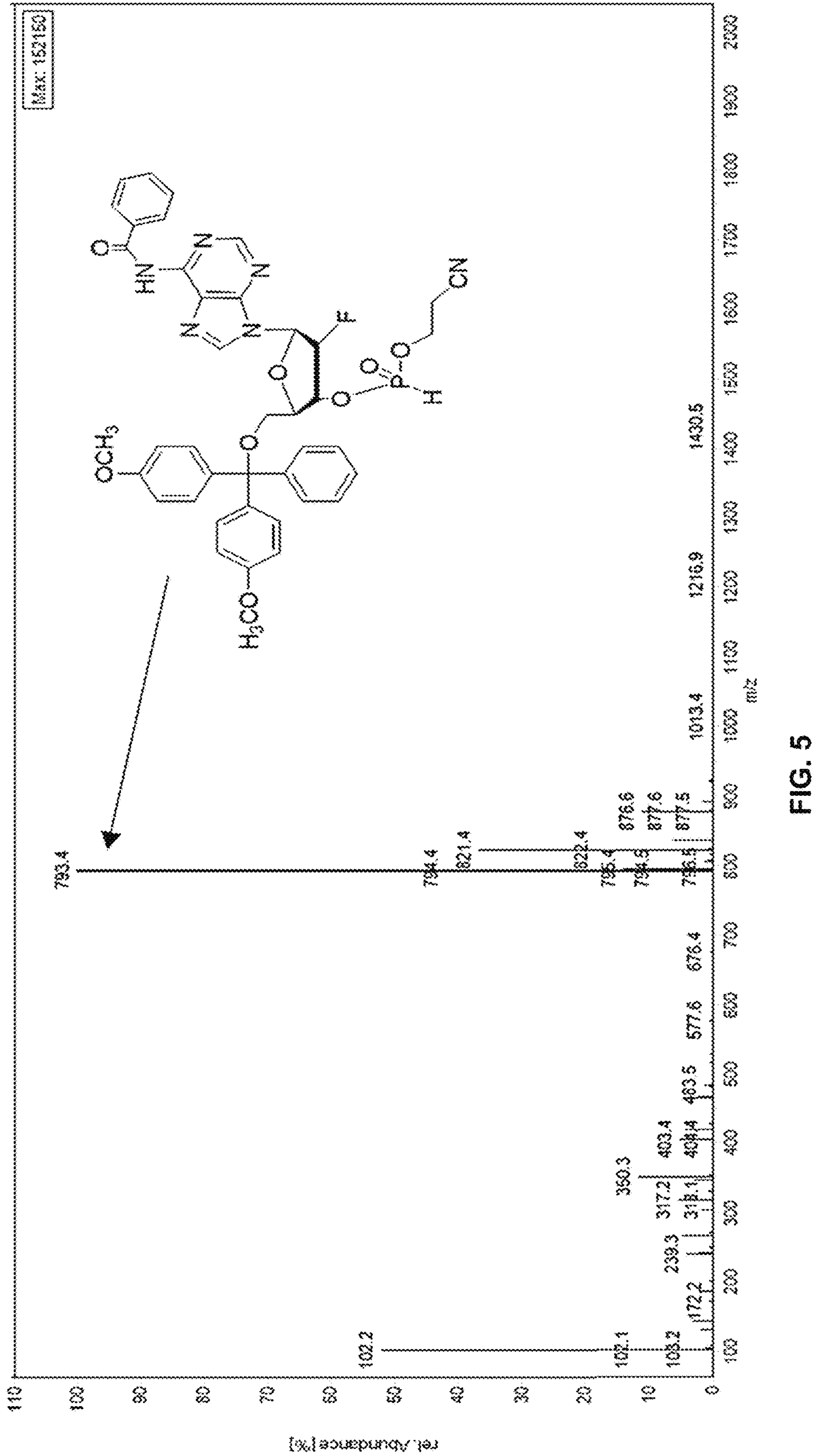
Figure 6:
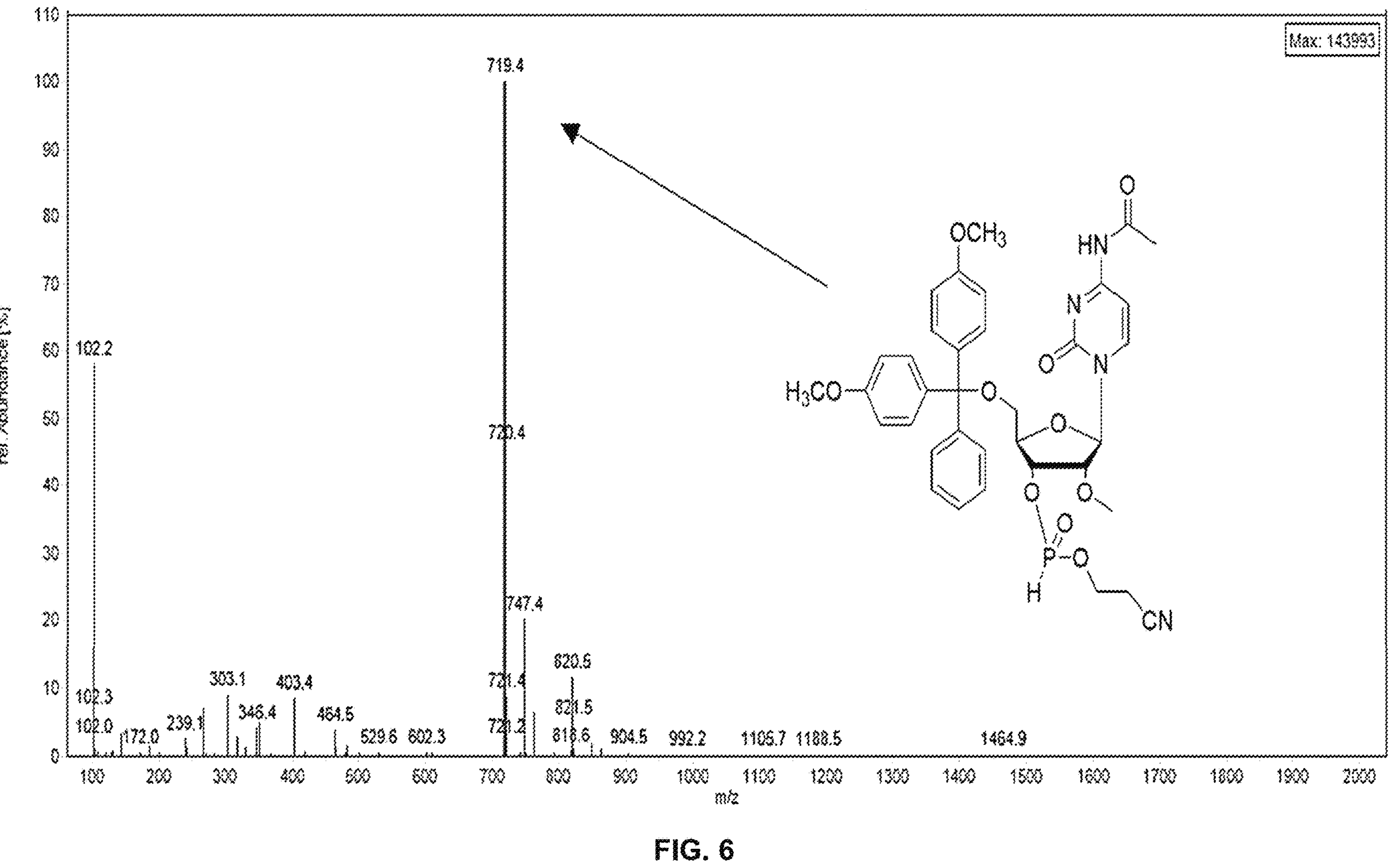
Figure 7:
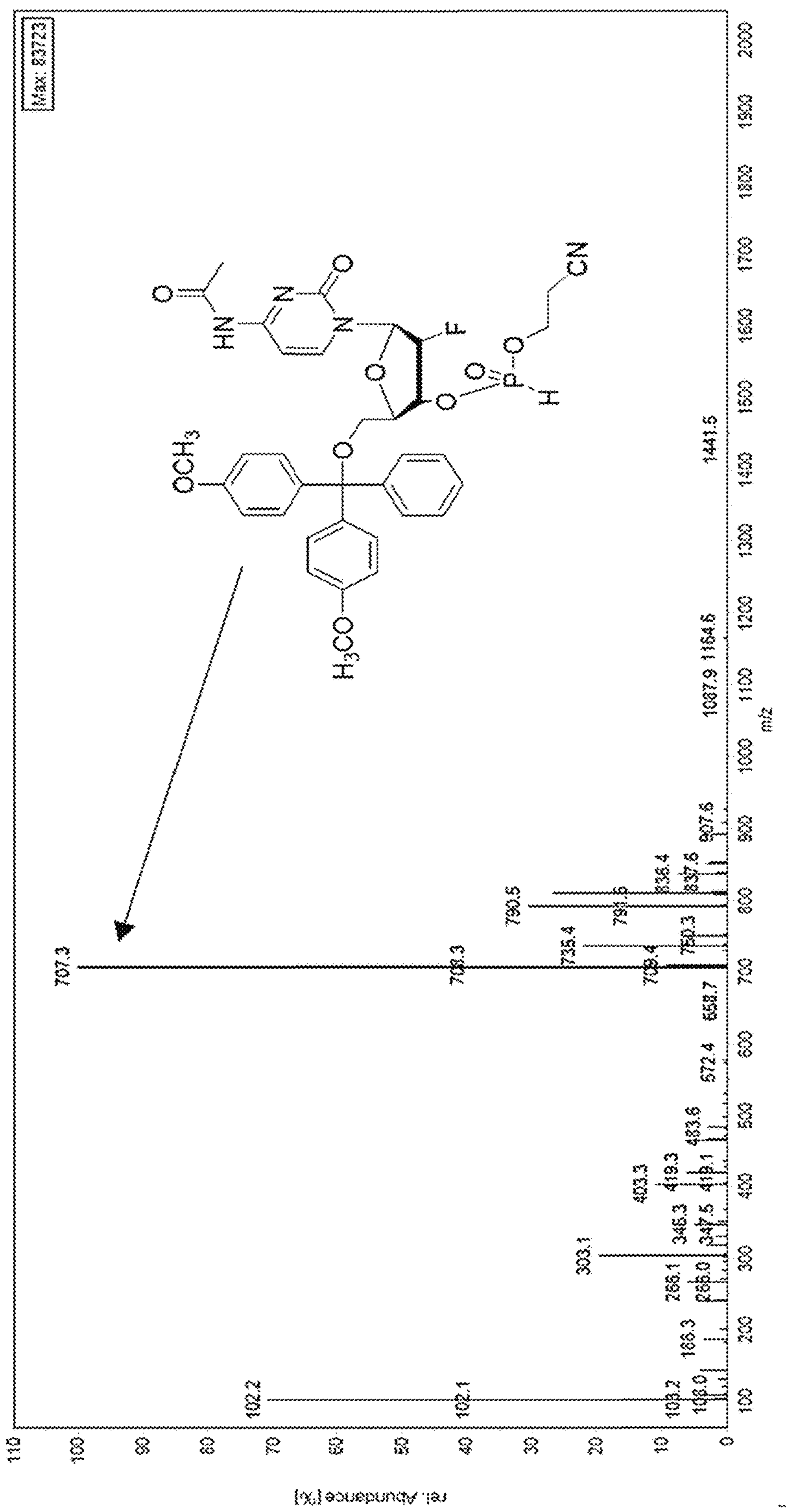
Figure 8:
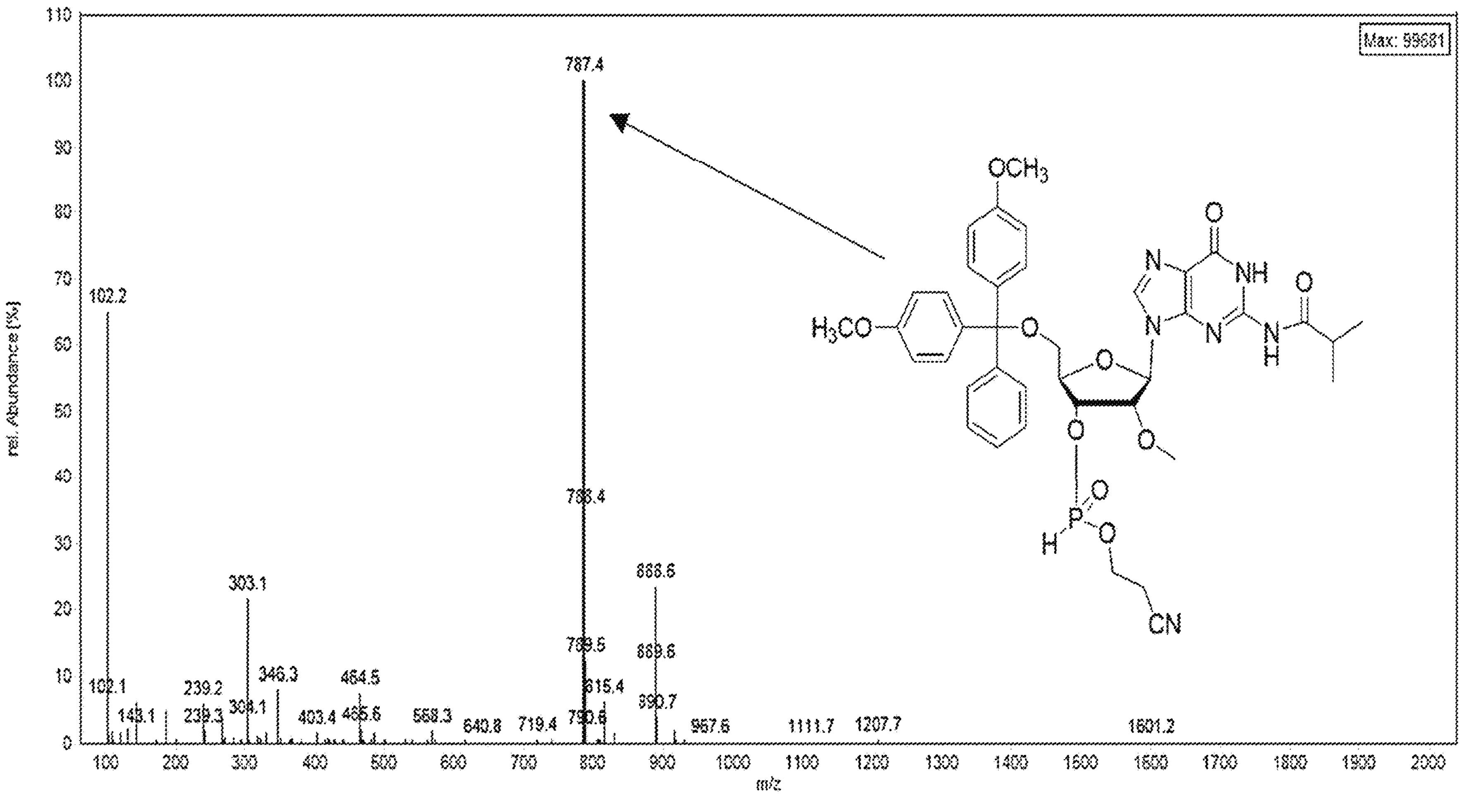
Figure 9:
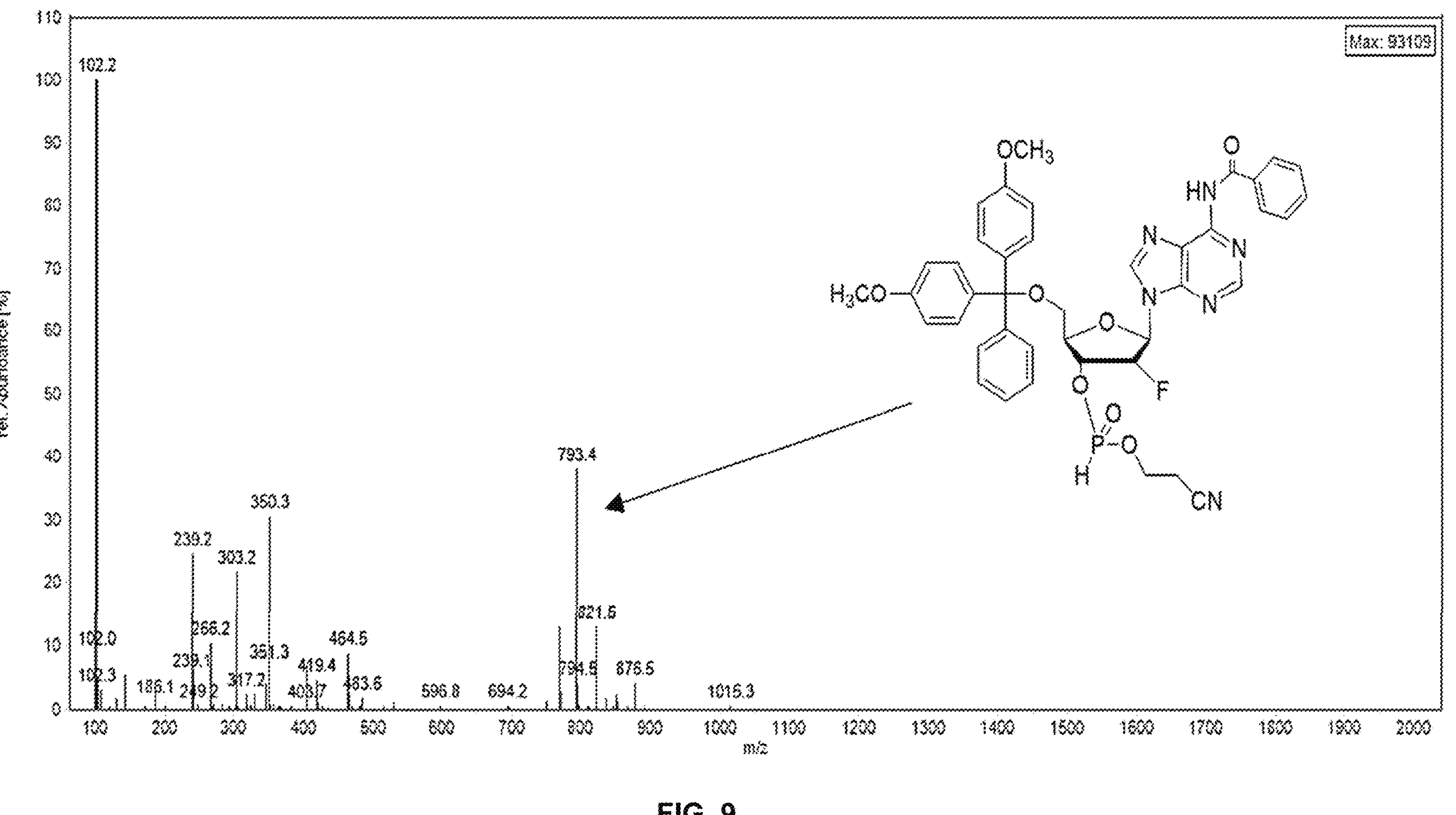
Figure 10:
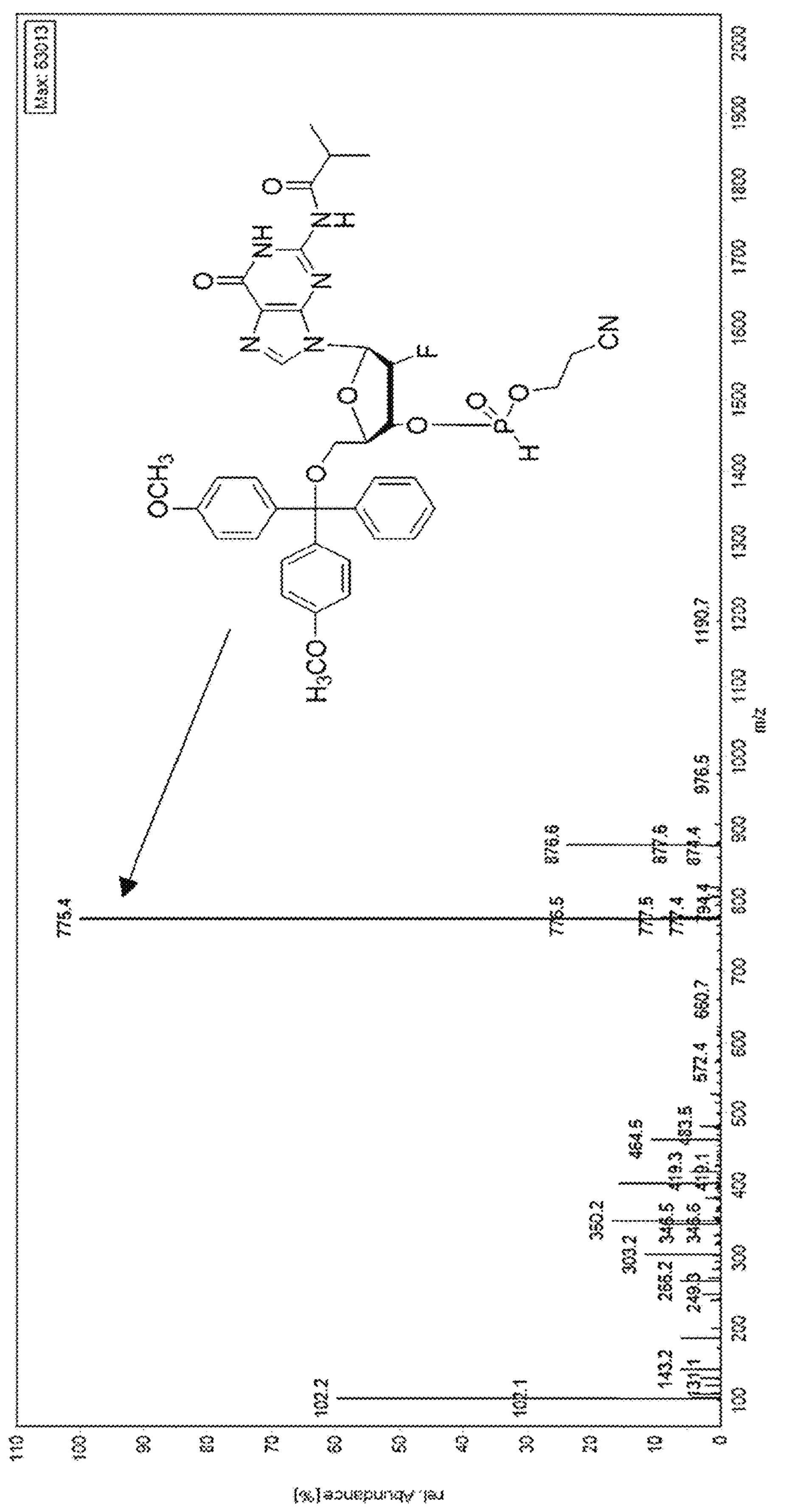
Figure 11:
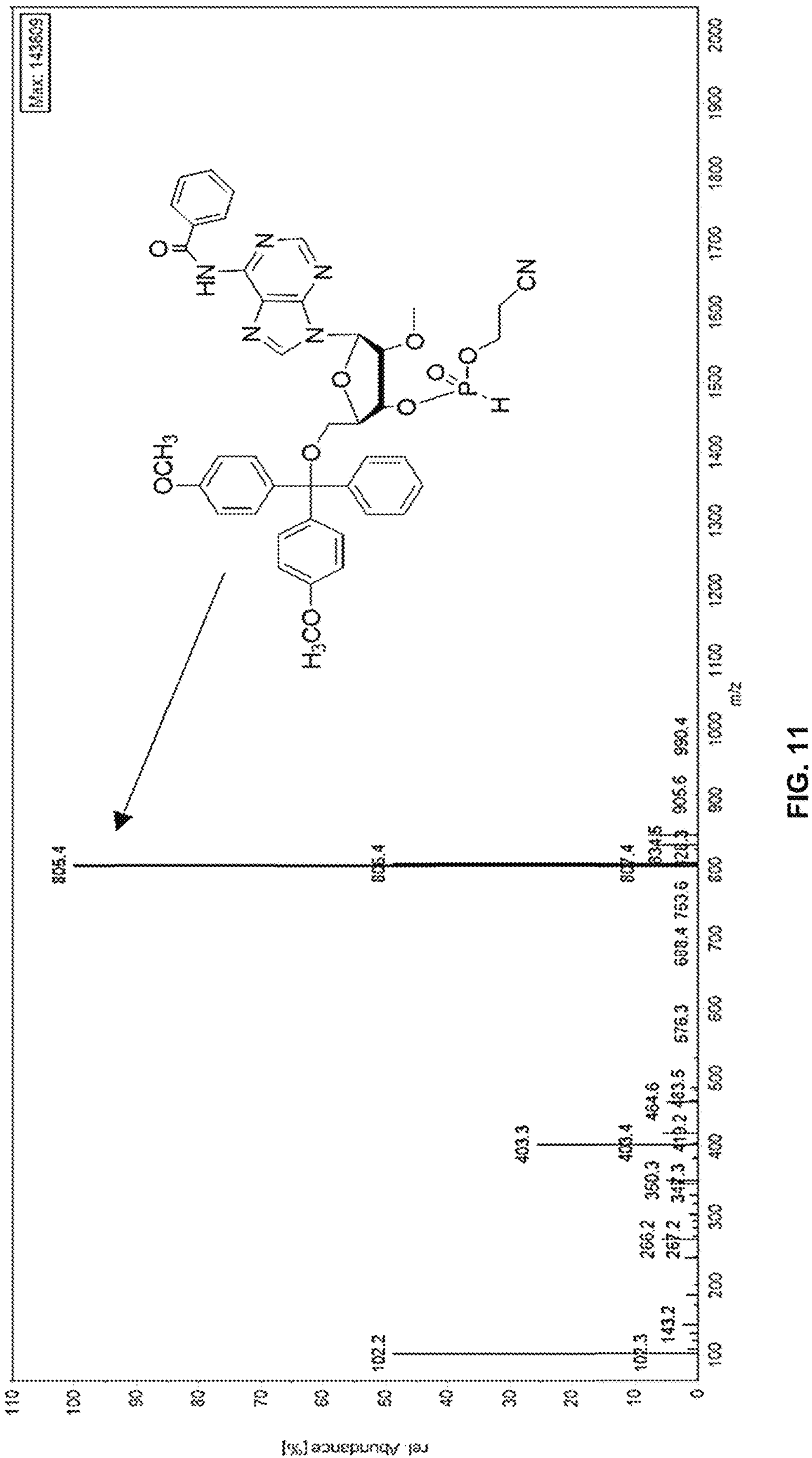

FIG. 5 shows mass spectral data from Sample 1-2 with theoretical chemical structure (fA). FIG. 6 shows mass spectral data from Sample 1-3 with theoretical chemical structure (mC). FIG. 7 shows mass spectral data from Sample 1-4 with theoretical chemical structure (fC). FIG. 8 shows mass spectral data from Sample 1-5 with theoretical chemical structure (mG). FIG. 9 shows mass spectral data from Sample 1-6 with theoretical chemical structure (fA). FIG. 10 shows mass spectral data from Sample 1-7 with theoretical chemical structure (fG). FIG. 11 shows mass spectral data from Sample 1-8 with theoretical chemical structure (mA).

Each position of the 8-mer RNA sequence was confirmed. The nucleotides were confirmed in the H-Phosphonate protected configuration.

Example 2

In this example, the nucleotide sequence was confirmed for an oligonucleotide containing seven nucleotides, including modified nucleotides. A 7-base ribonucleic acid (RNA) oligonucleotide sequence consisting of both 2'-fluoro and 2'-methoxy RNA nucleotides was synthesized with the NCEV system connected to the reaction chamber. The solid phase synthesis was carried out as described in Example 1. The samples were automatically diluted post-sample injection using a Flow Modulator.

The setup of the reaction chamber was the same as listed under the General Methods section.

Sample creation and analysis was performed with a customized Agilent 1290 UHPLC consisting of three (3) analytical pumps (Sample, Mobile Phase, and Flow Modulator Pumps), a Flow Modulator, a custom On-line sample manager (AS) with an external valve, and an Agilent 6135XT single quadrupole MSD. The sample was collected neat by the AS. Post sample injection, the sample was diluted by the Flow Modulator using 0.1% Formic Acid+50% ACN. The Mobile Phase Pump solution was 0.1% Formic Acid+50% ACN. The instrument parameters utilized are listed in Table 4.

TABLE 4

| UHPLC-MS method parameters | |
|---|---|
| **HPLC Parameters** | |
| Sample Pump Flow Rate | 3.0 mL/min |
| Mobile Phase Pump Flow Rate (Main Flow) | 0.2 mL/min |
| Flow Modulator Pump Flow Rate (Makeup Flow) | 0.2 mL/min |
| Flow Modulator Split Rate | 10:1 |
| Flow Modulator Dilution Factor | 1:10 |
| Injection Volume | 2.0 μL |
| Stoptime | 1 min |
| **Single Quadrupole MSD Parameters** | |
| Ionization Mode | ESI |
| Polarity | Positive |
| Drying Gas Temperature | 300° C. |
| Drying Gas Flow Rate | 11 L/min |
| Nebulizer | 28 psig |
| Capillary Voltage | 3500 V |
| Mass Range | 100-2000 m/z |
| Dwell Time | 800 ms |
| Fragmentor | 10 V |
| Gain | 1 |

Nucleotides were conjugated in the following order: 3'-fAmCfCmGfAfGmA-5'. Each nucleotide addition was collected and analyzed. The experimental data is shown in Table 5 and FIGS. 12 to 18.

TABLE 5

Experimental Data from Example 2

| Sample Number | Mass Observed | Theoretical Positive mode Free Acid mass (+1H) | Absolute Difference from Theoretical Positive Mode Mass | Proposed Species by Mass | Actual Species | Confirmed? |
|---|---|---|---|---|---|---|
| 2-1 | 793.4 | 793.3 | 0.1 | fA | fA | Yes |
| 2-2 | 719.4 | 719.7 | 0.3 | mC | mC | Yes |
| 2-3 | 707.4 | 707.2 | 0.2 | fC | fC | Yes |
| 2-4 | 787.4 | 787.3 | 0.1 | mG | mG | Yes |
| 2-5 | 793.4 | 793.3 | 0.1 | fA | fA | Yes |
| 2-6 | 775.4 | 775.3 | 0.1 | fG | fG | Yes |
| 2-7 | 805.4 | 805.3 | 0.1 | mA | mA | Yes |

Figure 12:
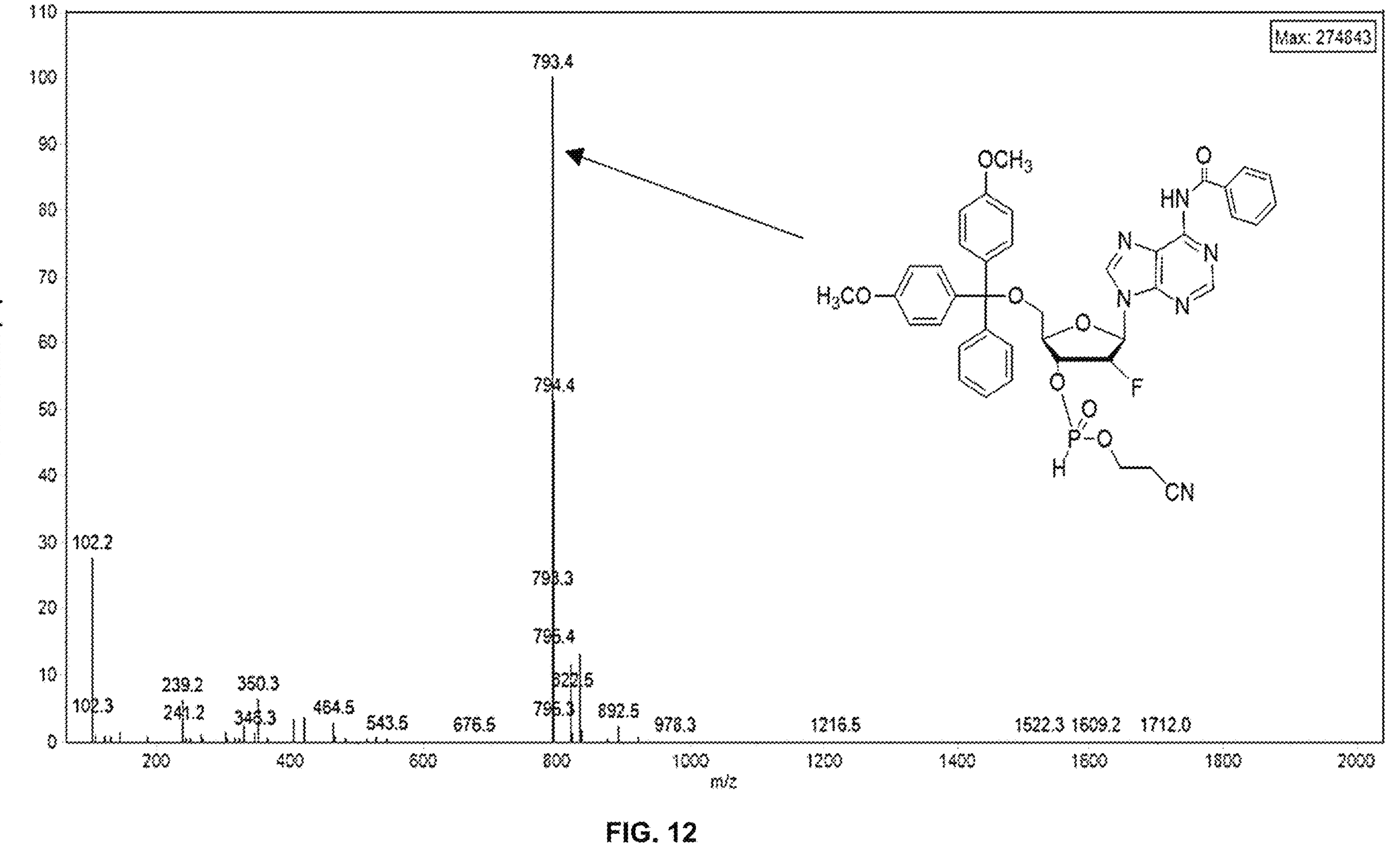
FIGS. 12 to 18 show mass spectral data from Samples 2-1 to 2-7, respectively, from Example 2.
Figure 13:
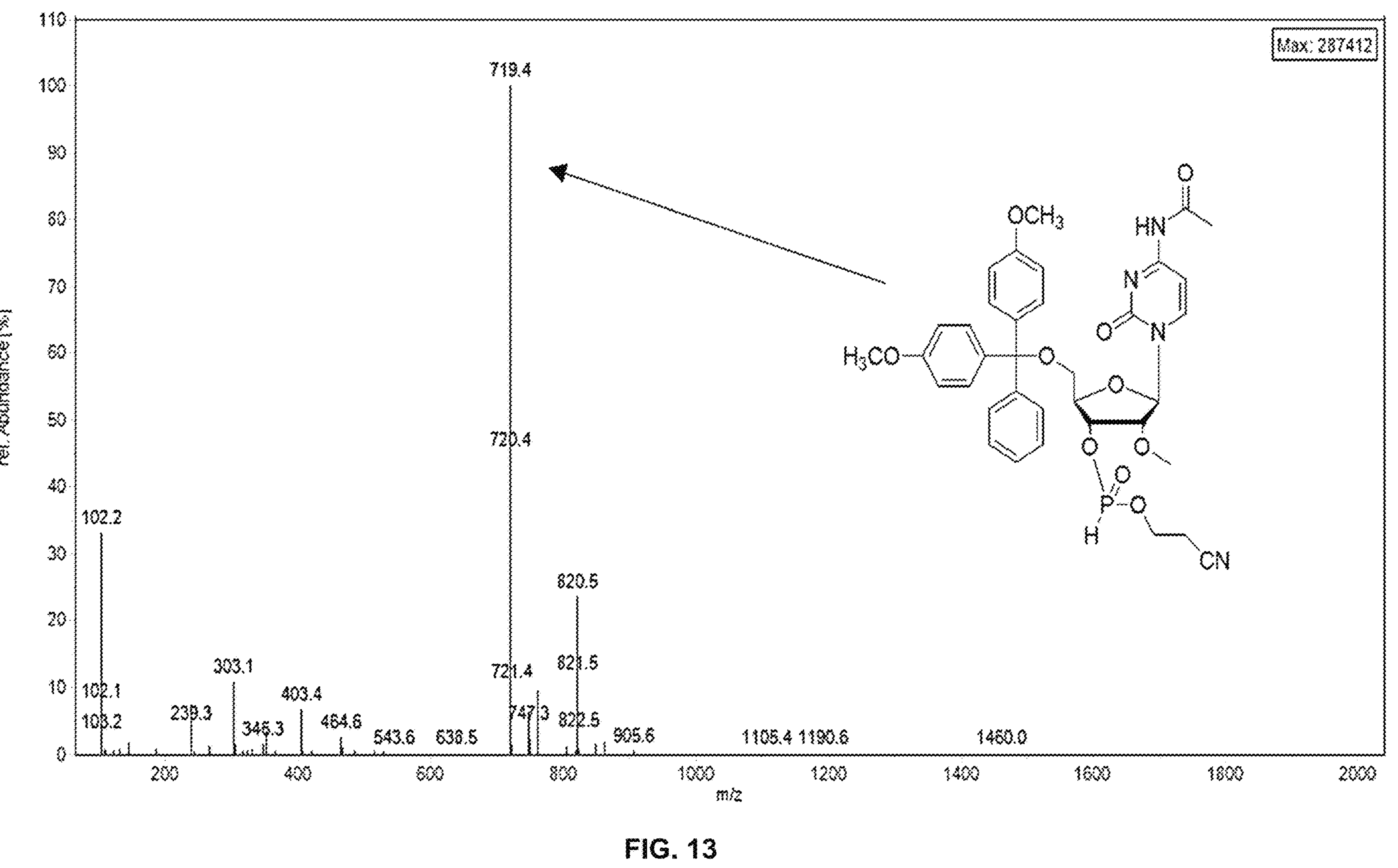
Figure 14:
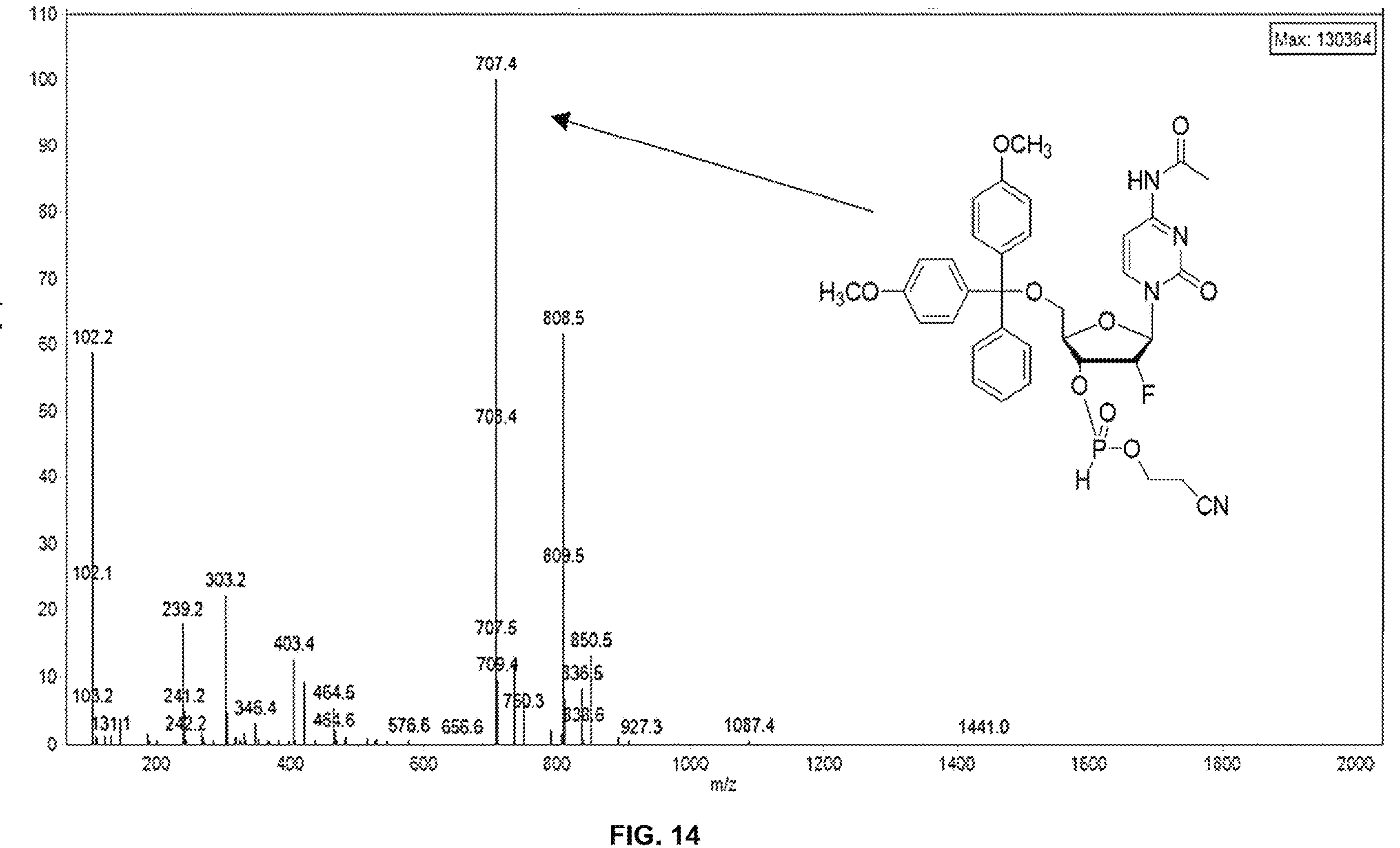
Figure 15:
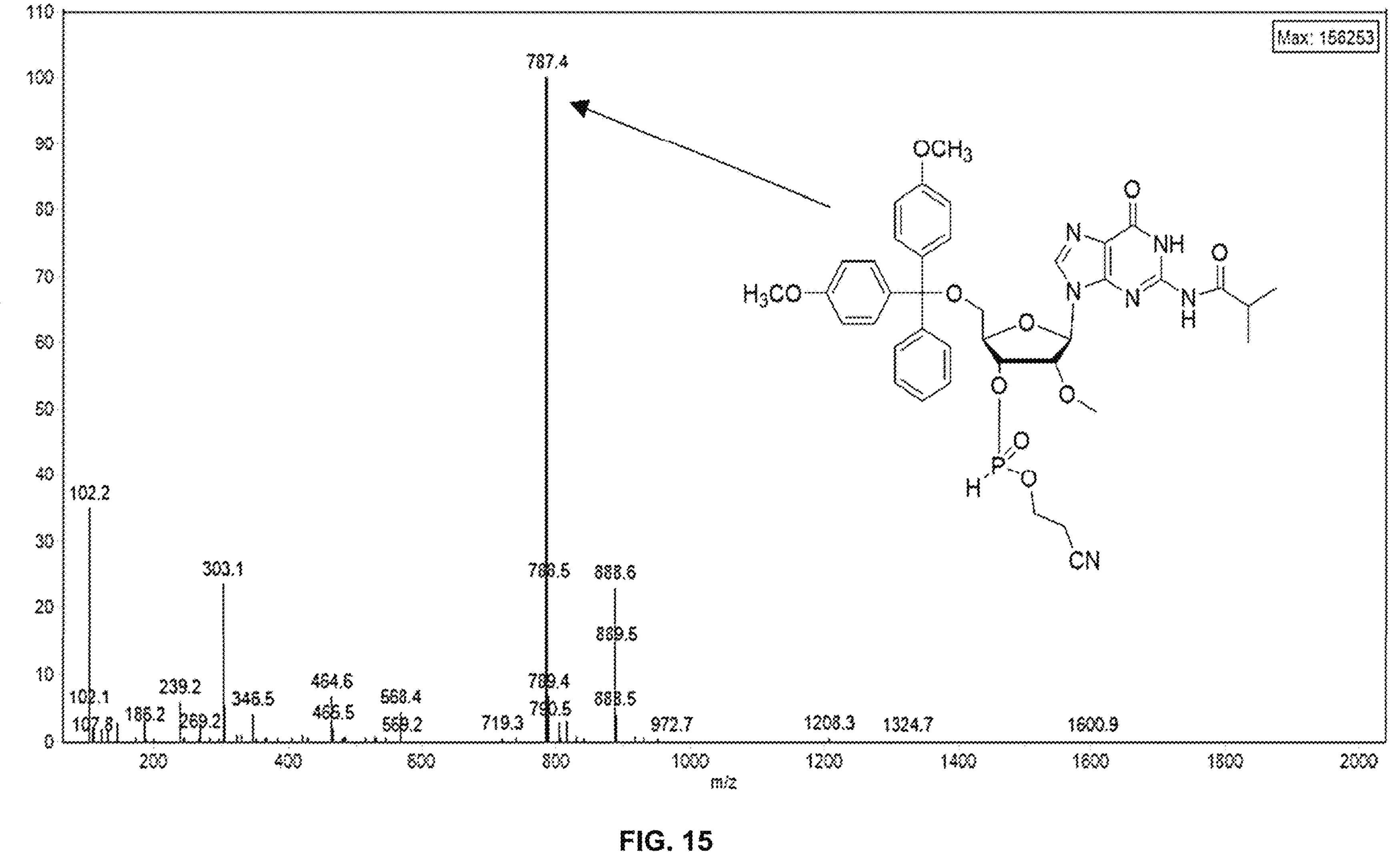
Figure 16:
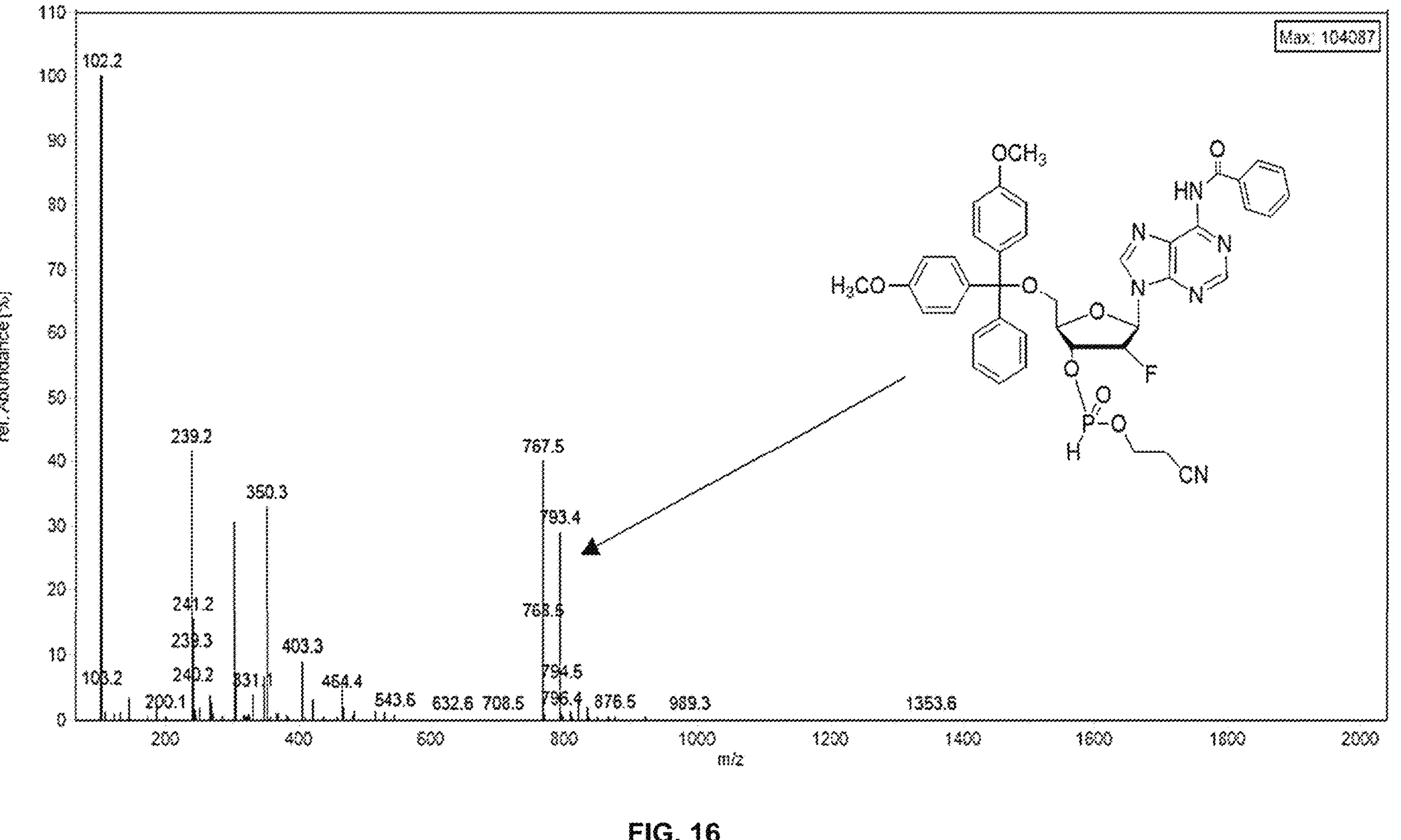
Figure 17:
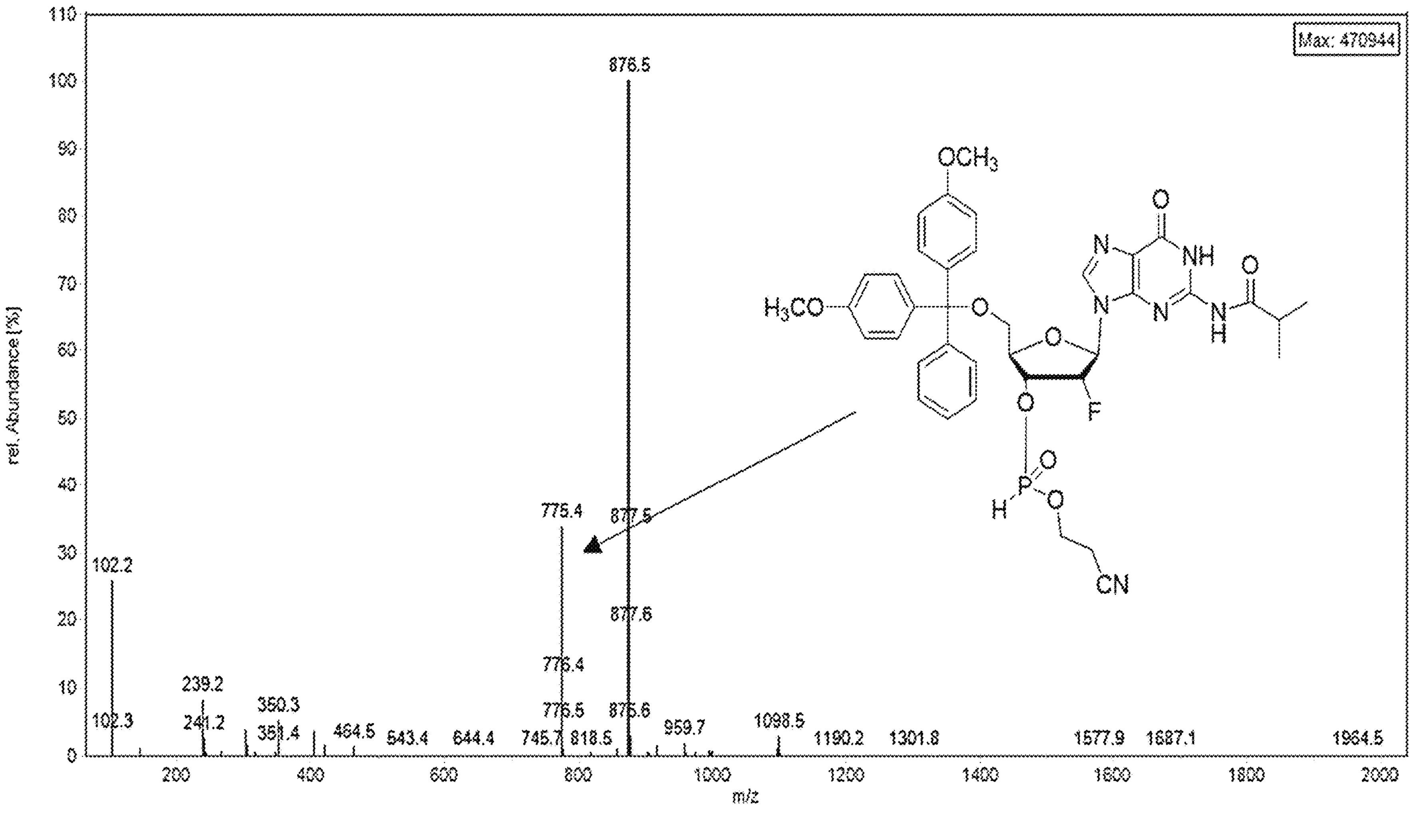
Figure 18:
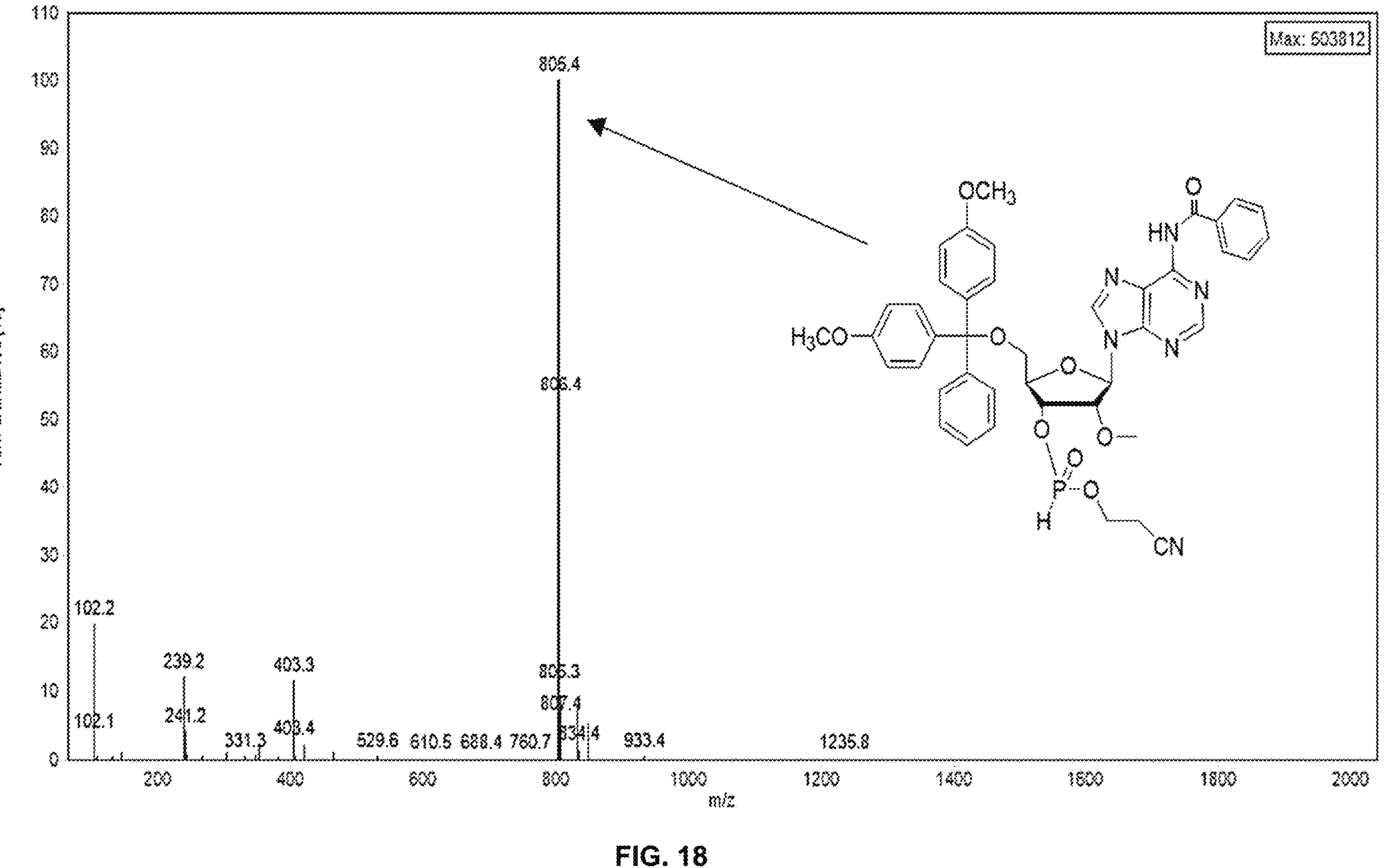

FIG. 12 shows mass spectral data from Sample 2-1 with theoretical chemical structure (fA). FIG. 13 shows mass spectral data from Sample 2-2 with theoretical chemical structure (mC). FIG. 14 shows mass spectral data from Sample 2-3 with theoretical chemical structure (fC). FIG. 15 shows mass spectral data from Sample 2-4 with theoretical chemical structure (mG). FIG. 16 shows mass spectral data from Sample 2-5 with theoretical chemical structure (fA). FIG. 17 shows mass spectral data from Sample 2-6 with theoretical chemical structure (fG). FIG. 18 shows mass spectral data from Sample 2-7 with theoretical chemical structure (mA).

Each position of the 7-mer RNA sequence was confirmed. The nucleotides were confirmed in the H-Phosphonate protected configuration.

EXEMPLARY EMBODIMENTS

Before various exemplary embodiments are described, it is to be understood that the teachings of this disclosure are not limited to the particular embodiments described, and as such can, of course, vary. Exemplary embodiments provided in accordance with the presently disclosed subject matter include, but are not limited to, the following:

Embodiment 1. A method of synthesizing an oligonucleotide and monitoring the synthesis in real time comprising: selecting a nucleotide monomer for addition to an oligonucleotide; feeding an inlet stream to a reaction chamber for oligonucleotide synthesis; provide conditions in the reaction chamber for oligonucleotide synthesis; diverging an outlet stream from the reaction chamber to an analysis station; analyzing the outlet stream or a sample thereof by mass spectrometry (MS) in the analysis station; and determining, based on results from analyzing by MS, whether the outlet stream comprises the selected nucleotide monomer or a derivative thereof.

Embodiment 2. The method of embodiment 1, further comprising stopping the feed of the inlet stream to the reaction chamber if it is determined that the outlet stream does not comprise the selected nucleotide monomer.

Embodiment 3. The method of embodiment 1 or embodiment 2, further comprising connecting a source of the selected nucleotide monomer to the inlet stream before the feeding step.

Embodiment 4. The method of any of embodiments 1 to 3, wherein the determining step is performed before a subsequent nucleotide monomer is fed to the reaction chamber.

Embodiment 5. The method of any of embodiments 1 to 4, further comprising applying timestamps to the results from analyzing by MS, associating the timestamps with feed times of the inlet stream to the reaction chamber, and using the timestamps and associated feed times to determine if the selected nucleotide monomer was present in the inlet stream.

Embodiment 6. The method of embodiment 5, comprising using the timestamps and the associated feed times to calculate a nucleotide sequence for the oligonucleotide synthesized in the reaction chamber.

Embodiment 7. The method of embodiment 6, further comprising distributing or approving the synthesized oligonucleotide if the calculated nucleotide sequence matches a predetermined nucleotide sequence.

Embodiment 8. The method of embodiment 6, further comprising withholding or rejecting the synthesized oligonucleotide if the calculated nucleotide sequence does not match the predetermined nucleotide sequence.

Embodiment 9. The method of any of embodiments 1 to 8, wherein the outlet stream or a sample thereof is analyzed by liquid chromatography/mass spectrometry (LC/MS).

Embodiment 10. The method of any of embodiments 1 to 9, wherein the MS analysis is performed with a low-resolution detector.

Embodiment 11. The method of any of embodiments 1 to 10, wherein the inlet stream is not analyzed for the selected nucleotide monomer before the feeding step.

Embodiment 12. The method of any of embodiments 1 to 11, wherein the oligonucleotide comprises ribonucleotides, deoxyribonucleotides, or a mixture thereof.

Embodiment 13. The method of embodiment 12, wherein the selected nucleotide monomer is a 3'-phosphoramidite ribonucleotide having protecting groups at 2'-, 5'- and nucleobase positions.

Embodiment 14. The method of embodiment 13, wherein the ribonucleotide has a 5'-dimethyltrityl protecting group and a 2'-protecting group selected from the group consisting of thionocarbamate (TC) protecting group, bis(2-acetoxyethoxy)methyl (ACE) protecting group, t-butyldimethylsilyl (TBDMS) protecting group, triisopropylsilyloxymethyl (TOM) protecting group, pivaloyloxymethyl (PivOM) protecting group and 2-cyanoethoxymethyl (CEM) protecting group.

Embodiment 15. The method of any of embodiments 1 to 14, wherein the selected nucleotide monomer is 793.3 Da, and the outlet stream is determined to comprise the selected nucleotide monomer if the MS detects a fragment having a molecular weight of 792.3-794.3 Da.

Embodiment 16. The method of any of embodiments 1 to 15, wherein the selected nucleotide monomer comprises a modified nucleobase.

Embodiment 17. A system for synthesizing an oligonucleotide comprising: a reaction chamber comprising an inlet, a solid support for oligonucleotide synthesis, and an outlet; and a mass spectrometry (MS) instrument fluidically connected to the outlet of the reaction chamber.

Embodiment 18. The system of embodiment 17, further comprising an on-line sample manager between the outlet of the reaction chamber and the MS instrument, whereby the on-line sample manager receives the outlet stream or a sample thereof from the reaction chamber and delivers the outlet stream or a sample thereof to the MS instrument.

Embodiment 19. The system of embodiment 17 or 18, further comprising a sample pump between the reaction chamber and the on-line sample manager Embodiment 20. The system of any of embodiments 17 to 19, further comprising a flow modulator valve between the on-line sample manager and the MS instrument.

Embodiment 21. The system of any of embodiments 17 to 20, wherein the solid support is a planar substrate or a bead.

Embodiment 22. The system of any of embodiments 17 to 21, further comprising one or more computing devices communicably connected with the reaction chamber, the on-line sample manager, and the MS instrument, wherein the one or more computing devices comprises a processor and a storage medium, and the processor is configured to execute instructions stored on the storage medium to: determine, based on data from the MS instrument, if whether an outlet stream from the reaction chamber comprises a selected nucleotide monomer or a derivative thereof.

Embodiment 23. The system of embodiment 22, wherein the one or more computing devices is further configured to: control conditions within the reaction chamber; start and/or stop the feeding of an inlet stream to the reaction chamber; and/or activate and/or deactivate the on-line sample manager.

Embodiment 24. The system of any of embodiments 17 to 23, further comprising a sensor at the outlet of the reaction chamber, wherein the sensor detects presence or absence of nucleotide monomer in a diluent.

Embodiment 25. The system of embodiment 24, wherein the sensor is communicably connected with the one or more computing devices, and the one or more computing devices is further configured to direct the outlet stream to the on-line sample manager and/or to activate the on-line sample manager, if the sensor detects the presence of a nucleotide monomer in the outlet stream.

Embodiment 26. The system of any of embodiments 17 to 25, wherein the MS instrument is a low-resolution MS instrument.

In view of this disclosure it is noted that the methods any systems can be implemented in keeping with the present teachings. Further, the various components, materials, structures and parameters are included by way of illustration and example only and not in any limiting sense. In view of this disclosure, the present teachings can be implemented in other applications and components, materials, structures and equipment to implement these applications can be determined, while remaining within the scope of the appended claims.

We claim:

1. A method of synthesizing an oligonucleotide and monitoring the synthesis of the oligonucleotide in real time comprising:

selecting a nucleotide monomer for addition to an oligonucleotide;

feeding an inlet stream to a reaction chamber for oligonucleotide synthesis, wherein the inlet stream comprises the selected nucleotide monomer;

providing conditions in the reaction chamber for oligonucleotide synthesis;

diverging an outlet stream from the reaction chamber to an analysis station;

monitoring the oligonucleotide synthesis in real time using a computing device comprising a processor and a storage medium, wherein the processor is programmed to execute instructions stored on the storage medium to analyze whether the outlet stream comprises the selected nucleotide monomer or a derivative thereof, the monitoring comprises:

analyzing the outlet stream or a sample thereof by a mass spectrometry (MS) instrument in the analysis station with the computing device communicably connected with the MS instrument;

and determining, based on results from analyzing by MS, whether the outlet stream comprises the selected nucleotide monomer or a derivative thereof thereby confirming the selected nucleotide monomer was fed in the inlet stream to the reaction chamber in a proper order and as intended by a predetermined sequence of the oligonucleotide to be synthesized.

2. The method of claim 1, further comprising:

stopping the feed of the inlet stream to the reaction chamber if it is determined that the outlet stream does not comprise the selected nucleotide monomer.

3. The method of claim 1, further comprising connecting a source of the selected nucleotide monomer to the inlet stream before the feeding step.

4. The method of claim 1, wherein the determining step is performed before a subsequent nucleotide monomer is fed to the reaction chamber.

5. The method of claim 1, further comprising applying timestamps to the results from analyzing by MS, associating the timestamps with feed times of the inlet stream to the reaction chamber, and using the timestamps and associated feed times to determine if the selected nucleotide monomer was present in the inlet stream.

6. The method of claim 5, comprising using the timestamps and the associated feed times to calculate a nucleotide sequence for the oligonucleotide synthesized in the reaction chamber.

7. The method of claim 6, further comprising distributing or approving the synthesized oligonucleotide if the calculated nucleotide sequence matches the predetermined sequence of the oligonucleotide to be synthesized.

8. The method of claim 6, further comprising withholding or rejecting the synthesized oligonucleotide if the calculated nucleotide sequence does not match the predetermined sequence of the oligonucleotide to be synthesized.

9. The method of claim 1, wherein the outlet stream or a sample thereof is analyzed by liquid chromatography/mass spectrometry (LC/MS).

10. The method of claim 1, wherein the MS analysis is performed with a low-resolution detector.

11. The method of claim 1, wherein the inlet stream is not analyzed for the selected nucleotide monomer before the feeding step.

12. The method of claim 1, wherein the oligonucleotide comprises ribonucleotides, deoxyribonucleotides, or a mixture thereof.

13. The method of claim 12, wherein the selected nucleotide monomer is a 3'-phosphoramidite ribonucleotide having protecting groups at 2'-, 5'- and nucleobase positions.

14. The method of claim 13, wherein the 3'-phosphoramidite ribonucleotide has a 5'-dimethyltrityl protecting group and a 2'-protecting group selected from the group consisting of thionocarbamate (TC) protecting group, bis(2-acetoxyethoxy)methyl (ACE) protecting group, t-butyldimethylsilyl (TBDMS) protecting group, triisopropylsilyloxymethyl (TOM) protecting group, pivaloyloxymethyl (PivOM) protecting group and 2-cyanoethoxymethyl (CEM) protecting group.

15. The method of claim 1, wherein the selected nucleotide monomer is 793.3 Da, and the outlet stream is determined to comprise the selected nucleotide monomer if the MS detects a fragment having a molecular weight of 792.3-794.3 Da.

16. The method of claim 1, wherein the selected nucleotide monomer comprises a modified nucleobase.

* * * * *